US009540617B2

(12) United States Patent
Yokoyama et al.

(10) Patent No.: US 9,540,617 B2
(45) Date of Patent: Jan. 10, 2017

(54) METHOD FOR PRODUCING HORSERADISH PEROXIDASE RECOMBINANT PROTEIN USING FILAMENTOUS FUNGUS

(71) Applicant: MEIJI SEIKA PHARMA CO., LTD., Tokyo (JP)

(72) Inventors: Fumikazu Yokoyama, Odawara (JP); Kaoru Okakura, Odawara (JP); Atsushi Inoue, Odawara (JP); Koichiro Murashima, Odawara (JP); Toshiaki Nagasato, Odawara (JP); Koji Yanai, Odawara (JP); Akitaka Nakane, Tokyo (JP)

(73) Assignee: MEIJI SEIKA PHARMA CO., LTD., Tokyo (JP)

( * ) Notice: Subject to any disclaimer, the term of this patent is extended or adjusted under 35 U.S.C. 154(b) by 240 days.

(21) Appl. No.: 14/404,076

(22) PCT Filed: May 30, 2013

(86) PCT No.: PCT/JP2013/064995
§ 371 (c)(1),
(2) Date: Nov. 26, 2014

(87) PCT Pub. No.: WO2013/180208
PCT Pub. Date: Dec. 5, 2013

(65) Prior Publication Data
US 2015/0140574 A1 May 21, 2015

(30) Foreign Application Priority Data

May 31, 2012 (JP) ................................. 2012-124598

(51) Int. Cl.
| | | |
|---|---|---|
| *C12Q 1/28* | (2006.01) | |
| *G01N 33/535* | (2006.01) | |
| *D06L 3/11* | (2006.01) | |
| *G01N 33/58* | (2006.01) | |
| *C12N 9/08* | (2006.01) | |

(52) U.S. Cl.
CPC .............. *C12N 9/0065* (2013.01); *C12Q 1/28* (2013.01); *C12Y 111/01007* (2013.01); *D06L 3/11* (2013.01); *G01N 33/535* (2013.01); *G01N 33/581* (2013.01)

(58) Field of Classification Search
None
See application file for complete search history.

(56) References Cited

U.S. PATENT DOCUMENTS

| | | | |
|---|---|---|---|
| 5,147,793 A | 9/1992 | Johnson et al. | |
| 2003/0041351 A1 | 2/2003 | Kasukabe et al. | |
| 2006/0105352 A1 | 5/2006 | Qiao et al. | |
| 2008/0118965 A1 | 5/2008 | Roubos et al. | |
| 2009/0280534 A1 | 11/2009 | Christensen et al. | |

FOREIGN PATENT DOCUMENTS

| | | |
|---|---|---|
| CN | 101107354 A | 1/2008 |
| EP | 0481815 A2 | 4/1992 |
| JP | 4-262785 A | 9/1992 |
| JP | 2008-523829 A | 7/2008 |
| JP | 2008-527985 A | 7/2008 |
| JP | 2010-183872 A | 8/2010 |
| WO | 0172999 A1 | 10/2001 |
| WO | 2006/077258 A1 | 7/2006 |
| WO | 2012/098246 A1 | 7/2012 |
| WO | 2013/015326 A1 | 1/2013 |

OTHER PUBLICATIONS

Smith et al. (J. Biol. Chem., 1990, vol. 265, pp. 13335-13343).*
Communication dated Oct. 9, 2015 from the State Intellectual Property Office of the P.R.C. in counterpart application No. 201380029041.7.
Fujiyama et al. "P00433.2" GenBank, Apr. 28, 2012. p. 1-12.
Database UniProtKB [Online], Apr. 18, 2012, "RecName: Peroxidase C1A (EC: 1.11.1.7) (history entry version 103)", XP-002753896, retrieved from UniProt Database accession No. P00433, 4 pgs. total.
Communication dated Feb. 29, 2016, issued by the European Patent Office in corresponding European Application No. 13798125.4.
International Preliminary Report on Patentability dated Dec. 2, 2014, with Written Opinion issued in International Application No. PCT/JP2013/064995.
Kazuhito Fujiyama et al., "Structure of the horseradish peroxidase isozyme C genes", Eur. J. Biochem. 1988, pp. 681-687, vol. 173.
Zhanglin Lin et al., "Functional Expression of Horseradish Peroxidase in *E. coli* by Directed Evolution", Biotechnol. Prog. 1999, pp. 467-471, vol. 15.
Andrew T. Smith et al., "Expression of a Synthetic Gene for Horseradish Peroxidase C in *Escherichia coli* and Folding and Activation of the Recombinant Enzyme with $Ca^{2+}$ and Heme", The Journal of Biological Chemistry 1990, pp. 13335-13343, vol. 265, No. 22, Issue of Aug. 5.
Birgit Morawski et al., "Functional expression of horseradish peroxidase in *Saccharomyces cerevisiae* and *Pichia pastoris*", Protein Engineering 2000, pp. 377-384, vol. 13, No. 5.
Takeshi Matsui et al., "High-Efficiency Secretory Production of Peroxidase C1a Using Vesicular Transport Engineering in Transgenic Tobacco", Journal of Bioscience and Bioengineering 2006, pp. 102-109, vol. 102, No. 2.

(Continued)

*Primary Examiner* — Suzanne M Noakes
*Assistant Examiner* — Jae W Lee
(74) *Attorney, Agent, or Firm* — Sughrue Mion, PLLC

(57) ABSTRACT

A modified polynucleotide has a different base sequence in at least one codon from a wild-type base sequence encoding a horseradish peroxidase polypeptide. The usage frequency of the modified codon of the polynucleotide corresponds to the codon usage frequencies of three filamentous fungal species in *Humicola*, *Aspergillus*, and *Trichoderma*. The polynucleotide is capable of expressing the polypeptide to be encoded in a filamentous fungus.

10 Claims, 14 Drawing Sheets

(56) References Cited

OTHER PUBLICATIONS

Valentino S.J. Te'o et al., "Codon optimization of xylanase gene *xynB* from the thermophilic bacterium *Dictyoglomus thermophilum* for expression in the filamentous fungus *Trichoderma reesei*", FEMS Microbiology Letters 2000, pp. 13-19, vol. 190, No. 1.

International Search Report for PCT/JP2013/064995 dated Aug. 27, 2013.
Extended European Search Report dated Jun. 17, 2016, from the European Patent Office in corresponding European Application No. 13798125.4.

* cited by examiner

Fig. 2

```
  1'  ATGCATTTCT CTTCTTCTTC TACTTTGTTC ACTTGTATAA CCTTAATCCC ATTGGTATGT
      ***** ****  *   ** **    **   * *** ** ** ** * ** * *****    * ** **
  1"  ATGCACTTCT CCAGCTCCTC CACCCTCTTC ACGTGCATCA CCCTCATCCC CCTCGTCTGC

61'  CTTATTCTTC ATGCTTCTTT GTCTGATGCT CAACTTACCC CTACCTTCTA CGACAATTCA
      ** ** ** * *  *****   * *** ** **   ** ** **** ********** ****** **
 61"  CTCATCCTCC ACGCTTCCCT GTCCGACGCC CAGCTCACCC CTACCTTCTA CGACAACTCC

121'  TGTCCTAATG TCTCTAACAT CGTACGGGAT ACTATTGTCA ATGAGCTAAG ATCAGACCCT
      ** ***** * **   ***** *** ** **   ** ** **** * *****   *  ** *****
121"  TGCCCTAACG TCAGCAACAT CGTCCGCGAC ACCATCGTCA ACGAGCTGCG CTCCGACCCC

181'  CGTATTGCCG CGAGCATCCT TCGTCTTCAC TTCCACGACT GCTTTGTTAA TGGTTGTGAC
      ***** ****  *   ******  ** ** *** ********** **** ** **    ***** ***
181"  CGTATCGCCG CCTCCATCCT CCGCCTCCAC TTCCACGACT GCTTCGTCAA CGGTTGCGAC

241'  GCATCGATCT TGTTAGACAA CACAACATCA TTTCGAACAG AGAAAGATGC GTTTGGAAAC
      ** ** ***   *  * ***** *** **    ** ** ** * ****  ** **   ** ** ***
241"  GCTTCCATCC TCCTCGACAA CACCACCAGC TTCCGCACCG AGAAGGACGC CTTCGGCAAC

301'  GCAAACTCGG CAAGAGGATT TCCAGTGATT GATAGAATGA AAGCCGCGGT GGAGAGTGCA
      ** *****  *  *  **  **    **  ** **    **  * **** * ***** **   ***    **
301"  GCCAACTCCG CTCGCGGCTT CCCCGTCATC GACCGCATGA AGGCCGCCGT CGAGTCCGCC

361'  TGCCCAAGAA CCGTTTCATG CGCAGATTTG CTCACCATTG CAGCTCAACA ATCTGTCACT
      *****   * *  ****    **  *** **  *  *****  ** * * ** ** **   ** *****
361"  TGCCCTCGCA CCGTCAGCTG CGCCGACCTC CTCACGATCG CCGCCCAGCA GTCCGTCACC

421'  TTGGCGGGAG GTCCTTCTTG GAGAGTTCCT TTGGGCAGAA GAGATAGCTT ACAAGCATTT
      * **  **  * *   ** **   ** **  * *  ******   * **    *     *  **    * *   ** ** **
421"  CTCGCCGGTG GCCCCTCCTG GCGTGTTCCT CTCGGTCGCC GCGACTCCCT CCAGGCTTTC

481'  CTGGATCTTG CTAATGCAAA TCTTCCAGCT CCATTCTTCA CACTTCCACA ACTTAAAGAC
      ** ** **  *  * ** ** **   ** ** ***  ** ******* *  ** ** **    ** ** ***
481"  CTCGACCTCG CCAACGCCAA CCTGCCCGCT CCCTTCTTCA CCCTGCCCCA GCTCAAGGAC
```

Fig. 3

```
541'  AGCTTTAGAA ATGTTGGCCT CAACCGTTCT TCTGATCTCG TTGCACTGTC CGGGGGCCAC
      ***   * * * ** ***** ****** **  ** ** **** **** ** ** *** ** ***
541"  TCCTTCCGCA ACGTCGGCCT CAACCGCTCC TCCGACCTCG TTGCCCTCTC CGGCGGTCAC

601'  ACATTTGGTA AAAATCAGTG TCGGTTTATT ATGGACAGAT TATACAACTT CAGCAACACC
      ** ** ** * * ** ***** ** ** ** ****** *   * ******** * *******
601"  ACCTTCGGCA AGAACCAGTG CCGCTTCATC ATGGACCGCC TCTACAACTT CTCCAACACC

661'  GGTTTACCCG ATCCTACTCT CAACACTACT TATCTCCAAA CTCTTCGTGG ACTATGTCCC
      **  * **** * ** ** ** ****** **    ** ** ** * ** ** **   ** ** ***
661"  GGCCTCCCCG ACCCCACCCT CAACACCACC TACCTGCAGA CCCTCCGCGG CCTCTGCCCC

721'  CTCAATGGTA ATCTAAGCGC TTTGGTGGAT TTTGATCTAC GTACGCCAAC GATTTTTGAC
      ***** ** * * **    ***   * ***** ** ** ** * * ** ** **   ** ** **
721"  CTCAACGGCA ACCTCTCCGC CCTCGTGGAC TTCGACCTCC GCACCCCCAC CATCTTCGAT

781'  AACAAATACT ATGTGAATCT CGAAGAGCAA AAAGGACTTA TCCAAAGCGA CCAAGAGTTG
      ***** **** * ** ** **  ** *****  ** ** ** * ****    *** *** *** **
781"  AACAAGTACT ACGTCAACCT GGAGGAGCAG AAGGGCCTCA TCCAGTCCGA CCAGGAGCTG

841'  TTCTCTAGCC CCAATGCCAC TGACACAATC CCTTTGGTGA GATCATTTGC TAATAGCACA
      *****    ** **** ***** ***** *** **  **** * ** ** ** ** ** ***
841"  TTCTCCTCCC CCAACGCCAC CGACACGATC CCCCTGGTCC GCTCCTTCGC CAACTCCACC

901'  CAAACATTCT TCAATGCATT TGTGGAGGCG ATGGATAGGA TGGGAAACAT TACACCTCTT
      ** ** **** **** ** **  ** *****  *****  * * **** ***** ** ** **
901"  CAGACGTTCT TCAACGCCTT CGTCGAGGCC ATGGACCGCA TGGGCAACAT CACCCCCCTC

961'  ACAGGAACTC AAGGACAGAT CAGGTTGAAT TGTAGGGTGG TGAACTCCAA CTCT
      ** ** ** * * ** ***** * *  * **   **   * ** * * ******** ***
961"  ACCGGCACCC AGGGCCAGAT CCGCCTCAAC TGCCGCGTCG TCAACTCCAA CTCC
```

Fig. 10

```
  1' ATGCATTTCT CTTCTTCTTC TACTTTGTTC ACTTGTATAA CCTTAATCCC ATTGGTATGT
     ***** ****  *   ** **   **   * *** ** ** ** * ** * *****   * ** **
  1" ATGCACTTCT CCAGCTCCTC CACCCTCTTC ACGTGCATCA CCCTCATCCC CCTCGTCTGC

61' CTTATTCTTC ATGCTTCTTT GTCTGATGCT CAACTTACCC CTACCTTCTA CGACAATTCA
     ** ** ** * * *****  * *** ** **  ** ** **** ********** ****** **
 61" CTCATCCTCC ACGCTTCCCT GTCCGACGCC CAGCTGACCC CTACCTTCTA CGACAACTCC

121' TGTCCTAATG TCTCTAACAT CGTACGGGAT ACTATTGTCA ATGAGCTAAG ATCAGACCCT
     ** ***** * **** ***** *** ** **  ** ** **** * *****   *  ** *****
121" TGCCCTAACG TCTCCAACAT CGTCCGCGAC ACCATCGTCA ACGAGCTCCG CTCCGACCCC

181' CGTATTGCCG CGAGCATCCT TCGTCTTCAC TTCCACGACT GCTTTGTTAA TGGTTGTGAC
     ***** ****  * ********  ** ** *** ********** **** ** **  ***** ***
181" CGTATCGCCG CCAGCATCCT CCGCCTCCAC TTCCACGACT GCTTCGTCAA CGGTTGCGAC

241' GCATCGATCT TGTTAGACAA CACAACATCA TTTCGAACAG AGAAAGATGC GTTTGGAAAC
     ** ** ***  *  * ***** *** **      ** ** ** * **** ** **  ** ** ***
241" GCTTCCATCC TCCTCGACAA CACCACCAGC TTCCGCACCG AGAAGGACGC CTTCGGCAAC

301' GCAAACTCGG CAAGAGGATT TCCAGTGATT GATAGAATGA AAGCCGCGGT GGAGAGTGCA
     ** *****  * *  * ** **   ** ** **  **  * **** * *****  ** ***    **
301" GCCAACTCCG CTCGCGGCTT CCCCGTCATC GACCGCATGA AGGCCGCCGT CGAGTCCGCC

361' TGCCCAAGAA CCGTTTCATG CGCAGATTTG CTCACCATTG CAGCTCAACA ATCTGTCACT
     *****  * * **** ** ** *** **   *  ***** ** * * ** ** **  ** *****
361" TGCCCTCGCA CCGTCTCCTG CGCCGACCTC CTCACGATCG CCGCCCAGCA GTCCGTCACC

421' TTGGCGGGAG GTCCTTCTTG GAGAGTTCCT TTGGGCAGAA GAGATAGCTT ACAAGCATTT
     * ** ** * * **    ** * * ****** * **  *     * **  * *  ** ** **
421" CTCGCCGGTG GCCCCAGCTG GCGTGTTCCT CTCGGTCGCC GCGACTCCCT CCAGGCTTTC

481' CTGGATCTTG CTAATGCAAA TCTTCCAGCT CCATTCTTCA CACTTCCACA ACTTAAAGAC
     ** ** ** * * * ** ** **  ** **  *** ** ******* * ** ** **  ** ** ***
481" CTCGACCTCG CCAACGCCAA CCTGCCCGCT CCCTTCTTCA CCCTGCCCCA GCTCAAGGAC
```

Fig. 11

```
541' AGCTTTAGAA ATGTTGGCCT CAACCGTTCT TCTGATCTCG TTGCACTGTC CGGGGGCCAC
     ***  *  *  * ** *****  ****** **   ** ** ****  **** ** ** *** ** ***
541" TCCTTCCGCA ACGTCGGCCT CAACCGCTCC TCCGACCTCG TTGCCCTCTC CGGCGGTCAC

601' ACATTTGGTA AAAATCAGTG TCGGTTTATT ATGGACAGAT TATACAACTT CAGCAACACC
     ** ** **  * * ** *****  ** ** **  ****** *   * ******** *  *******
601" ACCTTCGGCA AGAACCAGTG CCGCTTCATC ATGGACCGCC TCTACAACTT CTCCAACACC

661' GGTTTACCCG ATCCTACTCT CAACACTACT TATCTCCAAA CTCTTCGTGG ACTATGTCCC
     **  * **** * ** ** ** ****** **  ** ** ** * * ** ** **   ** ** ***
661" GGCCTCCCCG ACCCCACCCT CAACACCACC TACCTGCAGA CCCTCCGCGG CCTCTGCCCC

721' CTCAATGGTA ATCTAAGCGC TTTGGTGGAT TTTGATCTAC GTACGCCAAC GATTTTTGAC
     ***** ** *  * **   ***   * ***** ** ** ** * * ** ** **   ** ** **
721" CTCAACGGCA ACCTCTCCGC CCTCGTGGAC TTCGACCTCC GCACCCCCAC CATCTTCGAT

781' AACAAATACT ATGTGAATCT CGAAGAGCAA AAAGGACTTA TCCAAAGCGA CCAAGAGTTG
     ***** **** * ** ** **  ** *****  ** ** ** * ****   *** *** *** **
781" AACAAGTACT ACGTCAACCT GGAGGAGCAG AAGGGCCTCA TCCAGTCCGA CCAGGAGCTG

841' TTCTCTAGCC CCAATGCCAC TGACACAATC CCTTTGGTGA GATCATTTGC TAATAGCACA
     *****  ** **** *****  ***** *** **  ****   *  ** ** **  **    ***
841" TTCTCCTCCC CCAACGCCAC CGACACGATC CCCCTGGTCC GCTCCTTCGC CAACTCCACC

901' CAAACATTCT TCAATGCATT TGTGGAGGCG ATGGATAGGA TGGGAAACAT TACACCTCTT
     ** ** **** **** ** **   ** ***** *****  * * **** *****  ** ** **
901" CAGACGTTCT TCAACGCCTT CGTCGAGGCC ATGGACCGCA TGGGCAACAT CACCCCCCTC

961' ACAGGAACTC AAGGACAGAT CAGGTTGAAT TGTAGGGTGG TGAACTCCAA CTCT
     ** ** ** * ** *****  * *  * **   **  * ** * * ******** ***
961" ACCGGCACCC AGGGCCAGAT CCGCCTCAAC TGCCGCGTCG TCAACTCCAA CTCC
```

Fig. 12

```
  1' ATGCACTTCT CCAGCTCCTC CACCCTCTTC ACGTGCATCA CCCTCATCCC CCTCGTCTGC
     ********** ********** ********** ********** ********** **********
  1" ATGCACTTCT CCAGCTCCTC CACCCTCTTC ACGTGCATCA CCCTCATCCC CCTCGTCTGC

61' CTCATCCTCC ACGCTTCCCT GTCCGACGCC CAGCTCACCC CTACCTTCTA CGACAACTCC
     ********** ********** ********** ***** **** ********** **********
 61" CTCATCCTCC ACGCTTCCCT GTCCGACGCC CAGCTGACCC CTACCTTCTA CGACAACTCC

121' TGCCCTAACG TCAGCAACAT CGTCCGCGAC ACCATCGTCA ACGAGCTGCG CTCCGACCCC
     ******** ** ***** ********** ********** ****** ** **********
121" TGCCCTAACG TCTCCAACAT CGTCCGCGAC ACCATCGTCA ACGAGCTCCG CTCCGACCCC

181' CGTATCGCCG CCTCCATCCT CCGCCTCCAC TTCCACGACT GCTTCGTCAA CGGTTGCGAC
     ********** ** ****** ********** ********** ********** **********
181" CGTATCGCCG CCAGCATCCT CCGCCTCCAC TTCCACGACT GCTTCGTCAA CGGTTGCGAC

241' GCTTCCATCC TCCTCGACAA CACCACCAGC TTCCGCACCG AGAAGGACGC CTTCGGCAAC
     ********** ********** ********** ********** ********** **********
241" GCTTCCATCC TCCTCGACAA CACCACCAGC TTCCGCACCG AGAAGGACGC CTTCGGCAAC

301' GCCAACTCCG CTCGCGGCTT CCCCGTCATC GACGCATGA AGGCCGCCGT CGAGTCCGCC
     ********** ********** ******** ********* ********** **********
301" GCCAACTCCG CTCGCGGCTT CCCCGTCATC GACGCATGA AGGCCGCCGT CGAGTCCGCC

361' TGCCCTCGCA CCGTCAGCTG CGCCGACCTC CTCACGATCG CCGCCCAGCA GTCCGTCACC
     ********** ***** *** ********** ********** ********** **********
361" TGCCCTCGCA CCGTCTCCTG CGCCGACCTC CTCACGATCG CCGCCCAGCA GTCCGTCACC

421' CTCGCCGGTG GCCCCTCCTG GCGTGTTCCT CTCGGTCGCC GCGACTCCCT CCAGGCTTTC
     ********** ***** *** ********** ********** ********** **********
421" CTCGCCGGTG GCCCCAGCTG GCGTGTTCCT CTCGGTCGCC GCGACTCCCT CCAGGCTTTC

481' CTCGACCTCG CCAACGCCAA CCTGCCCGCT CCCTTCTTCA CCCTGCCCCA GCTCAAGGAC
     ********** ********** ********** ********** ********** **********
481" CTCGACCTCG CCAACGCCAA CCTGCCCGCT CCCTTCTTCA CCCTGCCCCA GCTCAAGGAC
```

Fig. 13

```
541'  TCCTTCCGCA ACGTCGGCCT CAACCGCTCC TCCGACCTCG TTGCCCTCTC CGGCGGTCAC
      ********** ********** ********** ********** ********** **********
541"  TCCTTCCGCA ACGTCGGCCT CAACCGCTCC TCCGACCTCG TTGCCCTCTC CGGCGGTCAC

601'  ACCTTCGGCA AGAACCAGTG CCGCTTCATC ATGGACCGCC TCTACAACTT CTCCAACACC
      ********** ********** ********** ********** ********** **********
601"  ACCTTCGGCA AGAACCAGTG CCGCTTCATC ATGGACCGCC TCTACAACTT CTCCAACACC

661'  GGCCTCCCCG ACCCCACCCT CAACACCACC TACCTGCAGA CCCTCCGCGG CCTCTGCCCC
      ********** ********** ********** ********** ********** **********
661"  GGCCTCCCCG ACCCCACCCT CAACACCACC TACCTGCAGA CCCTCCGCGG CCTCTGCCCC

721'  CTCAACGGCA ACCTCTCCGC CCTCGTGGAC TTCGACCTCC GCACCCCAC CATCTTCGAT
      ********** ********** ********** ********** ********** **********
721"  CTCAACGGCA ACCTCTCCGC CCTCGTGGAC TTCGACCTCC GCACCCCAC CATCTTCGAT

781'  AACAAGTACT ACGTCAACCT GGAGGAGCAG AAGGGCCTCA TCCAGTCCGA CCAGGAGCTG
      ********** ********** ********** ********* ********** **********
781"  AACAAGTACT ACGTCAACCT GGAGGAGCAG AAGGGCCTCA TCCAGTCCGA CCAGGAGCTG

841'  TTCTCCTCCC CCAACGCCAC CGACACGATC CCCCTGGTCC GCTCCTTCGC CAACTCCACC
      ********** ********** ********** ********** ********** **********
841"  TTCTCCTCCC CCAACGCCAC CGACACGATC CCCCTGGTCC GCTCCTTCGC CAACTCCACC

901'  CAGACGTTCT TCAACGCCTT CGTCGAGGCC ATGGACCGCA TGGGCAACAT CACCCCCCTC
      ********** ********** ********** ********** ********** **********
901"  CAGACGTTCT TCAACGCCTT CGTCGAGGCC ATGGACCGCA TGGGCAACAT CACCCCCCTC

961'  ACCGGCACCG AGGGCCAGAT CCGCCTCAAC TGCCGCGTCG TCAACTCCAA CTCCTAG
      ********** ********** ********** ********** ********** *******
961"  ACCGGCACCG AGGGCCAGAT CCGCCTCAAC TGCCGCGTCG TCAACTCCAA CTCCTAG
```

METHOD FOR PRODUCING HORSERADISH PEROXIDASE RECOMBINANT PROTEIN USING FILAMENTOUS FUNGUS

CROSS REFERENCE TO RELATED APPLICATIONS

This application is a National Stage of International Application No. PCT/JP2013/064995 filed May 30, 2013, claiming priority based on Japanese Patent Application No. 2012-124598 filed May 31, 2012, the contents of all of which are incorporated herein by reference in their entirety.

TECHNICAL FIELD

The present invention relates to a method for producing a horseradish (Armoracia rusticana) peroxidase recombinant protein using a filamentous fungus. Specifically, the present invention relates to a polynucleotide capable of encoding a peroxidase polypeptide derived from a horseradish and expressing the polypeptide in a filamentous fungus, an expression vector comprising the polynucleotide, a transformant of a filamentous fungus transformed with the expression vector introduced, a method for producing a horseradish peroxidase recombinant protein using the transformant, a horseradish peroxidase recombinant protein produced by the production method, and a preparation comprising the horseradish peroxidase recombinant protein, as well as uses of these.

BACKGROUND ART

Horseradish peroxidase is widely used as one of enzymes for detection in various tests such as enzyme-linked immunosorbent assay (ELISA), immunohistostaining method, Southern blotting method, and western blotting method. Moreover, the peroxidase has also been widely used as an enzyme for clinical inspection kits recently.

In general, peroxidases are widely present in the plant kingdom such as white radish (Raphanus sativus), sweet potato (Ipomoea batatas), wheat (Triticum spp.), Japanese horseradish (Eutrema japonica), and horseradish. For the reason that the peroxidase content in horseradish is high, or other reasons, horseradish is preferably used in industrial productions.

Meanwhile, horseradish peroxidase includes multiple enzymes such as acidic, neutral, and basic isozymes. Furthermore, the peroxidase content and the composition ratio of these isozymes greatly vary depending on: the properties of the soil where the horseradish is cultivated, the type and the amount of a fertilizer added, weather, harvesting time, and so forth. In addition, in a method for producing a peroxidase, a plant is destroyed and the peroxidase is purified from a great variety of contaminants. From the foregoing, the quality of a peroxidase purified from a horseradish is not always the same. In other words, most of horseradish peroxidase products used widely at present are mixtures of a large number of isozymes. In the majority of cases, the ratio is different from lot to lot. When such a horseradish peroxidase product is used to perform various measurements, for example, ELISA, a serious problem occurs that it is difficult to obtain stable measurement results because the results vary among production lots.

Moreover, horseradish that serves as the raw material requires a long period for cultivation and accordingly has a yield that varies depending on the weather. In addition, recently, a concern has been growing regarding a situation that horseradish supply might become short for reasons of: low cultivation efficiency, alternate farming to cereals for bioethanol having a higher demand, and the like. Hence, there is a great potential need for horseradish peroxidases that can be supplied steadily.

A conceivable method for overcoming the aforementioned problems of horseradish peroxidase is mass production by microorganisms using genetic recombination techniques. The use of microorganisms not only enables mass culture within a short period, but also enables steady supply without influence from the weather. Moreover, the use of genetic recombination techniques enables a single expression of a target peroxidase in a large amount. This makes it possible to avoid a problem of isozyme contamination.

The DNA sequence and the amino acid sequence of peroxidase C1a, one of main isozymes of horseradish peroxidase, have been revealed (see NPL 1). Moreover, using a gene encoding peroxidase C1a, the expression in Escherichia coli, yeast, and tobacco (Nicotiana tabacum) plant cells has been studied. However, the expression amount is as small as 0.11 mg/L in Escherichia coli (see NPL 2), 5.3 mg/L in yeasts (see NPL 3), and 3 mg/L in tobacco plant cells (see NPL 4). The productivity is quite low and impractical. From the foregoing, it has been desired to develop a recombinant organism capable of mass production of horseradish peroxidase, and a method for producing horseradish peroxidase using the recombinant organism.

CITATION LIST

Non Patent Literature

[NPL 1] Fujiyama et al., Eur. J. Biochem, 1988, vol. 173, pp. 681 to 687
[NPL 2] Lin et al., Biotechnol. Prog., 1999, vol. 15, pp. 467 to 471
[NPL 3] Morawski et al., Protein Engineering, 2000, vol. 13, pp. 377 to 384
[NPL 4] Matsui et al., J. Biosci. Bioeng., 2006, vol. 102, pp. 102 to 109

SUMMARY OF INVENTION

Technical Problem

The present invention has been made in consideration of the above-described problems in the conventional techniques. An object of the present invention is to provide a polynucleotide enabling efficient mass production of a horseradish peroxidase polypeptide.

Solution to Problem

In order to achieve the above object, the present inventors, first, introduced in a filamentous fungus an expression vector comprising a polynucleotide encoding wild-type horseradish peroxidase (HRP) C1a, and examined the amount of the HRP peptide produced in the obtained transformant. However, the inventors did not observe any production of the HRP peptide from the transformant, and revealed that even if the polynucleotide encoding the wild-type HRP polypeptide is used, no HRP polypeptide was produced in the filamentous fungus.

Hence, the present inventors have earnestly studied in order to express the HRP polypeptide in a filamentous fungus at a high level. First, the inventors took the codon usage frequencies of three filamentous fungal species in Humicola, Aspergillus, and Trichoderma into consideration. Next, the inventors prepared a codon-modified HRP polynucleotide such that codon occurrence frequencies in a HRP polynucleotide were adapted for the obtained codon usage frequencies. Then, Humicola, Aspergillus, and Trichoderma were transformed using this codon-modified HRP polynucleotide. As a result, although no expression was observed in Humicola, the expression of HRP was observed in Aspergillus and Trichoderma. Particularly, when Trichoderma was used, HRP was successfully produced at a concentration 100 times or more in comparison with the past.

Accordingly, in order to express HRP in Trichoderma at a high level, the present inventors transformed Trichoderma using a HRP polynucleotide adapted only for the codon usage frequencies of Trichoderma. As a result, the expression of HRP was observed in the transformant. However, surprisingly against expectations, the productivity of HRP was significantly higher in the case of the transformation using the polynucleotide modified in consideration of the codon usage frequencies of the three filamentous fungal species in Humicola, Aspergillus, and Trichoderma than in the case of the transformation using the polynucleotide adapted for the codon usage frequencies of only Trichoderma that served as the host cells.

In order to further verify the effectiveness of taking the codon usage frequencies of three filamentous fungal species in Humicola, Aspergillus, and Trichoderma into consideration, the present inventors prepared a different polynucleotide that was modified in consideration of the codon usage frequencies of the three filamentous fungal species, and transformed Trichoderma using the polynucleotide to evaluate the expression of HRP. As a result, a high level of a HRP expression was observed in transformed Trichoderma, similarly to the above. Further, it was revealed that the utilization of such a codon-modified HRP polynucleotide also enabled an expression of a HRP polypeptide in the filamentous fungus, the HRP polypeptide being fused with a His-tag polypeptide or a CBH1 polypeptide derived from Trichoderma. Furthermore, it was also found that these polypeptides fused with HRP made it possible to facilitate isolation and purification of HRP. Additionally, it was found that a HRP polypeptide produced by the transformed filamentous fungus with the codon-modified HRP polynucleotide was capable of discoloring an annatto pigment in the presence of hydrogen peroxide. These discoveries have led to the completion of the present invention. Specifically, the present invention more specifically provides the followings.

(1) A polynucleotide modified to have in at least one codon whose base sequence is different from a wild-type base sequence encoding a horseradish peroxidase polypeptide, having codon usage frequencies in the following percentages, and being capable of expressing the polypeptide to be encoded in a filamentous fungus, wherein in a case where an amino acid encoded by the modified codon is alanine, a usage frequency of GCC is 80% and a usage frequency of GCT is 20%;

in a case where the amino acid encoded by the modified codon is arginine, a usage frequency of CGC is 90% and a usage frequency of CGT is 10%;

in a case where the amino acid encoded by the modified codon is asparagine, a usage frequency of AAC is 100%;

in a case where the amino acid encoded by the modified codon is aspartic acid, a usage frequency of GAC is 95% and a usage frequency of GAT is 5%;

in a case where the amino acid encoded by the modified codon is cysteine, a usage frequency of TGC is 100%;

in a case where the amino acid encoded by the modified codon is glutamine, a usage frequency of CAG is 100%;

in a case where the amino acid encoded by the modified codon is glutamic acid, a usage frequency of GAG is 100%;

in a case where the amino acid encoded by the modified codon is glycine, a usage frequency of GGC is 75% and a usage frequency of GGT is 25%;

in a case where the amino acid encoded by the modified codon is histidine, a usage frequency of CAC is 100%;

in a case where the amino acid encoded by the modified codon is isoleucine, a usage frequency of ATC is 100%;

in a case where the amino acid encoded by the modified codon is leucine, a usage frequency of CTC is 80% and a usage frequency of CTG is 20%;

in a case where the amino acid encoded by the modified codon is lysine, a usage frequency of AAG is 100%;

in a case where the amino acid encoded by the modified codon is phenylalanine, a usage frequency of TTC is 100%;

in a case where the amino acid encoded by the modified codon is proline, a usage frequency of CCC is 80% and a usage frequency of CCT is 20%;

in a case where the amino acid encoded by the modified codon is serine, a usage frequency of AGC is 15% and a usage frequency of TCC is 85%;

in a case where the amino acid encoded by the modified codon is threonine, a usage frequency of ACC is 85% and a usage frequency of ACG is 15%;

in a case where the amino acid encoded by the modified codon is tyrosine, a usage frequency of TAC is 100%; and in a case where the amino acid encoded by the modified codon is valine, a usage frequency of GTC is 85%, a usage frequency of GTG is 5%, and a usage frequency of GTT is 10%.

(2) The polynucleotide according to (1), wherein at least two codons are modified.

(3) The polynucleotide according to any one of (1) and (2), wherein at least 10% of codons are modified.

(4) The polynucleotide according to any one of (1) to (3), which encodes a horseradish peroxidase C1a polypeptide and has at least one characteristic selected from the group consisting of the following (i) and (ii):

(i) comprising a coding region of a base sequence of SEQ ID NO: 1; and (ii) having a homology of 95% or more with a base sequence at positions 91 to 1017 of SEQ ID NO: 1.

(5) The polynucleotide according to any one of (1) to (3), which encodes a horseradish peroxidase C1a polypeptide and has at least one characteristic selected from the group consisting of the following (i) and (ii):

(i) comprising a coding region of a base sequence of SEQ ID NO: 26; and (ii) having a homology of 95% or more with a base sequence at positions 91 to 1017 of SEQ ID NO: 26.

(6) A polynucleotide comprising the polynucleotide according to anyone of (1) to (5), to which a polynucleotide encoding a desired polypeptide is added.

(7) An expression vector comprising the polynucleotide according to any one of (1) to (6).

(8) A transformant of a filamentous fungus transformed with the expression vector according to (7) introduced.

(9) The transformant according to (8), wherein the filamentous fungus is anyone of a fungus belonging to genus Trichoderma and a fungus belonging to genus Aspergillus.

(10) The transformant according to (8), wherein the filamentous fungus is any one of Trichoderma viride and Aspergillus niger.

(11) The transformant according to (8), wherein filamentous fungus is *Trichoderma viride*.

(12) A method for producing a polypeptide encoded by the polynucleotide according to any one of (1) to (6), the method comprising the steps of:

culturing the transformant according to any one of (8) to (11); and harvesting the polypeptide expressed from the cultured transformant and/or a culture of the transformant.

(13) A polypeptide produced by the method according to (12).

(14) A polypeptide produced by the method according to (12) and having a carbohydrate chain removed therefrom.

(15) A preparation comprising a polypeptide produced by the method according to (12).

(16) A method for detecting a target molecule, the method comprising binding of the target molecule to a polypeptide produced by the method according to (12).

(17) A method for discoloring a pigment, the method comprising causing a polypeptide produced by the method according to (12) to act on the pigment in presence of hydrogen peroxide.

(18) A method for removing a phenolic compound, the method comprising causing a polypeptide produced by the method according to (12) to act on the phenolic compound in presence of hydrogen peroxide.

Advantageous Effects of Invention

The present invention provides a polynucleotide encoding horseradish peroxidase and comprising codons optimized for expression in a filamentous fungus. Furthermore, the present invention makes it possible to produce a horseradish peroxidase recombinant protein by using *Trichoderma viride* or *Aspergillus niger* transformed with the polynucleotide.

BRIEF DESCRIPTION OF DRAWINGS

FIG. 2 is a figure for illustrating the result of comparing the base sequence (positions 1 to 540) between a wild-type HRP polynucleotide and a polynucleotide (codon-modified HRP polynucleotide) of the present invention. In the figure, upper sequences show the base sequence of the wild-type HRP polynucleotide (base sequence of SEQ ID NO: 3), and lower sequences show that of the polynucleotide of the present invention (base sequence of SEQ ID NO: 1).

FIG. 3 is a figure for illustrating the result of comparing the base sequence (positions 541 to 1014) between the wild-type HRP polynucleotide and the polynucleotide (codon-modified HRP polynucleotide) of the present invention. In the figure, upper sequences show the base sequence of the wild-type HRP polynucleotide (base sequence of SEQ ID NO: 3), and lower sequences show that of the polynucleotide of the present invention (base sequence of SEQ ID NO: 1).

FIG. 10 is a figure for illustrating the result of comparing the base sequence (positions 1 to 540) between the wild-type HRP polynucleotide and a polynucleotide (codon-modified HRP polynucleotide) of the present invention. In the figure, upper sequences show the base sequence of the wild-type HRP polynucleotide (base sequence of SEQ ID NO: 3), and lower sequences show that of the polynucleotide of the present invention (base sequence of SEQ ID NO: 26).

FIG. 11 is a figure for illustrating the result of comparing the base sequence (positions 541 to 1014) between the wild-type HRP polynucleotide and the polynucleotide (codon-modified HRP polynucleotide) of the present invention. In the figure, upper sequences show the base sequence of the wild-type HRP polynucleotide (base sequence of SEQ ID NO: 3), and lower sequences show that of the polynucleotide of the present invention (base sequence of SEQ ID NO: 26).

FIG. 12 is a figure for illustrating the result of comparing the base sequence (positions 1 to 540) between the polynucleotides of the present invention. In the figure, upper sequences show the base sequence of SEQ ID NO: 1, and lower sequences show the base sequence of SEQ ID NO: 26.

FIG. 13 is a figure for illustrating the result of comparing the base sequence (positions 541 to 1017) between the polynucleotides of the present invention. In the figure, upper sequences show the base sequence of SEQ ID NO: 1, and lower sequences show the base sequence of SEQ ID NO: 26.

DESCRIPTION OF EMBODIMENTS

Polynucleotide

Figure 1:
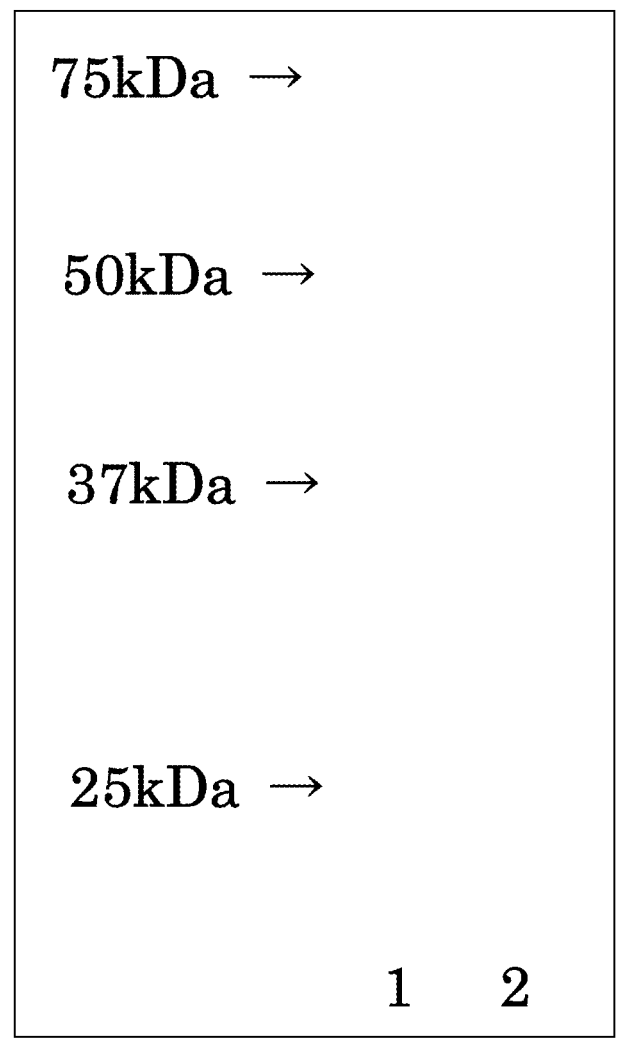
FIG. 1 is a photograph for illustrating the result of transforming a filamentous fungus (*Trichoderma*) with an expression vector (pCB1-HRP_Native) comprising a polynucleotide encoding wild-type horseradish peroxidase (HRP) C1a, and analyzing a culture supernatant of the resulting transformant by the western blot using an anti-HRP antibody. In the figure, lane 1 shows the result of spreading a molecular weight marker, and lane 2 shows the result of spreading the culture supernatant of the transformant.

As described in Examples later, in a western blot analysis, even if a polynucleotide having a wild-type base sequence encoding a horseradish peroxidase polypeptide (HRP) is used, no expression of a HRP polypeptide was detected in a filamentous fungus. However, the expression of the HRP polypeptide was detected in the filamentous fungus by using a polynucleotide modified to have a codon (s) whose base sequence is different from the wild-type base sequence.

Thus, the present invention provides the following polynucleotide.

A polynucleotide modified to have at least one codon whose base sequence is different from a wild-type base sequence encoding a horseradish peroxidase polypeptide, having codon usage frequencies in the following percentages, and being capable of expressing the polypeptide to be encoded in a filamentous fungus, wherein in a case where an amino acid encoded by the modified codon is alanine, a usage frequency of GCC is 80% and a usage frequency of GCT is 20%;

in a case where the amino acid encoded by the modified codon is arginine, a usage frequency of CGC is 90% and a usage frequency of CGT is 10%;

in a case where the amino acid encoded by the modified codon is asparagine, a usage frequency of AAC is 100%;

in a case where the amino acid encoded by the modified codon is aspartic acid, a usage frequency of GAC is 95% and a usage frequency of GAT is 5%;

in a case where the amino acid encoded by the modified codon is cysteine, a usage frequency of TGC is 100%;

in a case where the amino acid encoded by the modified codon is glutamine, a usage frequency of CAG is 100%;

in a case where the amino acid encoded by the modified codon is glutamic acid, a usage frequency of GAG is 100%;

in a case where the amino acid encoded by the modified codon is glycine, a usage frequency of GGC is 75% and a usage frequency of GGT is 25%;

in a case where the amino acid encoded by the modified codon is histidine, a usage frequency of CAC is 100%;

in a case where the amino acid encoded by the modified codon is isoleucine, a usage frequency of ATC is 100%;

in a case where the amino acid encoded by the modified codon is leucine, a usage frequency of CTC is 80% and a usage frequency of CTG is 20%;

in a case where the amino acid encoded by the modified codon is lysine, a usage frequency of AAG is 100%;

in a case where the amino acid encoded by the modified codon is phenylalanine, a usage frequency of TTC is 100%;

in a case where the amino acid encoded by the modified codon is proline, a usage frequency of CCC is 80% and a usage frequency of CCT is 20%;

in a case where the amino acid encoded by the modified codon is serine, a usage frequency of AGC is 15% and a usage frequency of TCC is 85%;

in a case where the amino acid encoded by the modified codon is threonine, a usage frequency of ACC is 85% and a usage frequency of ACG is 15%;

in a case where the amino acid encoded by the modified codon is tyrosine, a usage frequency of TAC is 100%; and in a case where the amino acid encoded by the modified codon is valine, a usage frequency of GTC is 85%, a usage frequency of GTG is 5%, and a usage frequency of GTT is 10%.

In the present invention, the term HRP polypeptide means an enzyme extracted from horseradish and having an activity of oxidatively cleaving and breaking down a peroxide structure into two hydroxyl groups. Examples thereof include isozymes HRP C1a, HRP C1b, HRP C1c, HRP C2, and HRP C3. A HRP C1a polypeptide is preferable from the viewpoint that it is an isozyme having the highest content among horseradish peroxidases, so that the properties thereof are reflected the most in the properties of a peroxidase mixture which is extracted from horseradish and is generally used as a reagent or the like.

Moreover, the HRP C1a polypeptide is typically a polypeptide comprising an amino acid sequence of SEQ ID NO: 4. Further, in nature also, an amino acid sequence may undergo mutation. Thus, the HRP polypeptide includes any polynucleotide encoding a protein comprising the amino acid sequence of SEQ ID NO: 4 in which one or more amino acids are substituted, deleted, inserted and/or added, as long as a protein having the above-described activity is encoded.

Note that, in the HRP C1a polypeptide, a polypeptide comprising residues from the methionine residue at the N-terminus to the 30th residue alanine is known to function as a signal peptide of HRP. Moreover, in the present invention, the term polypeptide means a molecule comprising two or more amino acids linked together by a peptide bond(s). Thus, the term is a concept including not only full-length proteins, but also so-called oligopeptides. Besides by a mutation of the amino acid sequence, the polypeptide may be modified, for example, by glycosylation, phosphorylation, palmitoylation, prenylation, methylation, acetylation, ubiquitination, SUMOylation, hydroxylation, amidation, and the like.

In the present invention, the term "wild-type base sequence encoding a HRP polypeptide" is typically a base sequence of SEQ ID NO: 3. The term "codon" means a combination of bases in three nucleotides encoding an amino acid.

In the present invention, at least one codon having a different base sequence from the wild-type base sequence is preferably a codon for improving a translation efficiency in a filamentous fungus. This codon is preferably a codon having a "degeneracy mutation" introduced without a change in the amino acid sequence.

When the amount of a HRP polypeptide produced by introducing into a filamentous fungus a polynucleotide modified to have at least one codon whose base sequence is different from the wild-type base sequence is larger than the amount of a HRP polypeptide produced by introducing into a filamentous fungus a polynucleotide having the wild-type base sequence, the codon can be determined as the "codon for improving a translation efficiency in a filamentous fungus." The amounts of HRP polypeptides can be compared as described in Examples later, for example, by employing known methods such as western blotting, detection of color development with tetramethylbenzidine (measurement of the absorbance at a wavelength of 450 nm), and measurement of the guaiacol oxidation activity.

Moreover, the number of codons modified is preferably at least two (for example, three or more, five or more), more preferably ten or more (for example, 20 or more, 30 or more, 50 or more), further preferably 100 or more (for example, 120 or more, 150 or more, 180 or more), and particularly preferably 200 or more (for example, 210 or more, 220 or more, 230 or more, 240 or more). Further, in the present invention, the ratio of the modified codons to all the codons in the polynucleotide having the wild-type base sequence is preferably at least 10%, more preferably 30% or more, and particularly preferably 60% or more (for example, 70% or more, 80% or more, 90% or more, 100%). Note that, among 338 codons in a coding region of abase sequence of SEQ ID NO: 1, 246 codons (72.8%) are modified (the degeneracy mutation is introduced). In addition, among 338 codons in a coding region of a base sequence of SEQ ID NO: 26, 245 codons (72.5%) are modified (the degeneracy mutation is introduced).

In the present invention, the term filamentous fungus means a fungus composed of hyphae. Examples of the filamentous fungus include fungi belonging to genus *Trichoderma*, fungi belonging to genus *Aspergillus*, fungi belonging to genus *Acremonium*, fungi belonging to genus *Fusarium*, fungi belonging to genus *Myceliopthora*, fungi belonging to genus *Neurospora*, fungi belonging to genus *Penicillium*, fungi belonging to genus *Rhizomucor*, fungi belonging to genus *Thermomyces*, fungi belonging to genus *Thielavia*, and fungi belonging to genus *Tolypocladium*.

Furthermore, more specifically, examples of the fungi belonging to the genus *Trichoderma* include *Trichoderma viride*, *Trichoderma harzianum*, *Trichoderma koningii*, *Trichoderma longibrachiatum*, and *Trichoderma reesei*. Moreover, examples of the fungi belonging to the genus *Aspergillus* include *Aspergillus niger*, *Aspergillus awamori*, *Aspergillus foetidus*, *Aspergillus japonicus*, *Aspergillus nidulans*, and *Aspergillus oryzae*. Among these, preferable are fungi belonging to the genera *Trichoderma* and *Aspergillus*, and more preferable are *Trichoderma viride* and *Aspergillus niger*.

In the present invention, the phrase "capable of expressing the polypeptide to be encoded" in such a filamentous fungus means that a concentration of HRP produced in a culture supernatant is 0.001 mg/L or more, preferably 1 mg/L or more, more preferably 10 mg/L or more, further preferably 100 mg/L or more, and particularly preferably 300 mg/L or more, where the culture supernatant is obtained by culturing a filamentous fungus transformed by introducing therein the polynucleotide modified to have at least one codon whose base sequence is different from the wild-type base sequence encoding a HRP polypeptide, and the culture supernatant is diluted in such a manner that a concentration of the transformant is $9 \times 10^8$ CFU/mL.

As described in Examples later, codon usage frequencies shown in Table 1 later were calculated in consideration of codon usage frequencies of three species in *Humicola*, *Aspergillus*, and *Trichoderma*. Then, the codon occurrence frequencies in the wild-type HRP polynucleotide were adapted for the obtained codon usage frequencies. The base sequence of the wild-type HRP polynucleotide (base sequence of SEQ ID NO: 3) was altered to the base sequence of SEQ ID NO: 1 or the base sequence of SEQ ID NO: 26. Subsequently, the codon-modified HRP polynucleotide thus prepared was used to transform a filamentous fungus. As a result, an expression of a HRP polypeptide was detected in spite of the fact that no expression of the HRP polypeptide was observed using the wild-type HRP polynucleotide.

Thus, a polynucleotide of the present invention is a polynucleotide encoding a HRP polypeptide and modified to have codon usage frequencies in the following percentages, wherein in a case where an amino acid encoded by the modified codon is alanine, a usage frequency of GCC is 80% and a usage frequency of GCT is 20%;

in a case where the amino acid encoded by the modified codon is arginine, a usage frequency of CGC is 90% and a usage frequency of CGT is 10%;

in a case where the amino acid encoded by the modified codon is asparagine, a usage frequency of AAC is 100%;

in a case where the amino acid encoded by the modified codon is aspartic acid, a usage frequency of GAC is 95% and a usage frequency of GAT is 5%;

in a case where the amino acid encoded by the modified codon is cysteine, a usage frequency of TGC is 100%;

in a case where the amino acid encoded by the modified codon is glutamine, a usage frequency of CAG is 100%;

in a case where the amino acid encoded by the modified codon is glutamic acid, a usage frequency of GAG is 100%;

in a case where the amino acid encoded by the modified codon is glycine, a usage frequency of GGC is 75% and a usage frequency of GGT is 25%;

in a case where the amino acid encoded by the modified codon is histidine, a usage frequency of CAC is 100%;

in a case where the amino acid encoded by the modified codon is isoleucine, a usage frequency of ATC is 100%;

in a case where the amino acid encoded by the modified codon is leucine, a usage frequency of CTC is 80% and a usage frequency of CTG is 20%;

in a case where the amino acid encoded by the modified codon is lysine, a usage frequency of AAG is 100%;

in a case where the amino acid encoded by the modified codon is phenylalanine, a usage frequency of TTC is 100%;

in a case where the amino acid encoded by the modified codon is proline, a usage frequency of CCC is 80% and a usage frequency of CCT is 20%;

in a case where the amino acid encoded by the modified codon is serine, a usage frequency of AGC is 15% and a usage frequency of TCC is 85%;

in a case where the amino acid encoded by the modified codon is threonine, a usage frequency of ACC is 85% and a usage frequency of ACG is 15%;

in a case where the amino acid encoded by the modified codon is tyrosine, a usage frequency of TAC is 100%; and in a case where the amino acid encoded by the modified codon is valine, a usage frequency of GTC is 85%, a usage frequency of GTG is 5%, and a usage frequency of GTT is 10%.

In the present invention, phrases such as "the wild-type HRP base sequence is modified to have the codon usage frequencies in the above percentages" means to include not only that the codon usage frequencies match the values of the above percentages per se, but also that the codon usage frequencies are adapted within a 2.5% range from the values of the percentages. For example, in the case where the amino acid encoded by the modified codon is serine, the phrase means that, in the base sequence of the polynucleotide encoding a HRP polypeptide, the codon encoding serine is altered to have such adapted usage frequencies that the usage frequency of AGC is 12.5 to 17.5%, and the usage frequency of TCC is 82.5 to 87.5%. Meanwhile, in the polynucleotide of the present invention, the number of amino acids with the codon usage frequencies in the aforementioned percentages should be at least one, but is preferably at least two (for example, three or more, five or more, seven or more), more preferably ten or more (for example, 12 or more, 15 or more, 17 or more), and particularly preferably all of 18 amino acids mentioned above.

As described above, as a result of transforming a filamentous fungus by using the polynucleotide having the base sequence modified to have the codon usage frequencies in the above percentages (the base sequence of SEQ ID NO: 1 or the base sequence of SEQ ID NO: 26), an expression of a HRP polypeptide was detected at a significantly high level.

Thus, the present invention provides a polynucleotide which encodes a horseradish peroxidase (HRP) C1a polypeptide and has at least one characteristic selected from the group consisting of the following (i) and (ii):

(i) comprising a coding region of a base sequence of SEQ ID NO: 1; and (ii) having a homology of 95% or more with a base sequence at positions 91 to 1017 of SEQ ID NO: 1.

Moreover, the present invention provides a polynucleotide which encodes a horseradish peroxidase (HRP) C1a polypeptide and has at least one characteristic selected from the group consisting of the following (i) and (ii):

(i) comprising a coding region of a base sequence of SEQ ID NO: 26; and (ii) having a homology of 95% or more with a base sequence at positions 91 to 1017 of SEQ ID NO: 26.

In the present invention, the "base sequence at positions 91 to 1017 of SEQ ID NO: 1" and the "base sequence at positions 91 to 1017 of SEQ ID NO: 26" each specifically mean a base sequence modified to have the codon usage frequencies in the above percentages and further to encode the HRP C1a polypeptide, from which a base sequence encoding a signal sequence is excluded.

Moreover, the term "homology" with regard to base sequence is used as a meaning of the degree of correspondence, between sequences to be compared, in bases constituting each sequence. Each of the numerical values of "homology" described in the present description may be any numerical value calculated using a homology search program known to those skilled in the art, and can be easily calculated by using the default (initial setting) parameters in FASTA, BLAST, Smith-Waterman, etc., for example.

Further, in order that the HRP C1a polypeptide demonstrates its activity, no signal sequence is required. Accordingly, in the polynucleotide of the present invention, a polynucleotide encoding the signal sequence (base sequence corresponding to positions 1 to 90 of SEQ ID NO: 1) may be excluded from the HRP polynucleotide.

Those skilled in the art can prepare the polynucleotide of the present invention by employing known techniques as appropriate. For example, as described in Examples later, the polynucleotide of the present invention can be chemically synthesized using a commercially-available DNA synthesizer on the basis of information on a base sequence designed to have a different base sequence in at least one codon from the wild-type base sequence encoding a HRP polypeptide. Alternatively, the polynucleotide of the present invention can be prepared by well-known methods such as site-directed mutagenesis to introduce a mutation (base substitution) into the wild-type HRP polynucleotide.

As described in Examples later, it has also been revealed that utilizing the codon-modified HRP polynucleotide makes it possible to express in a filamentous fungus a HRP polypeptide fused with a His tag polypeptide or a CBH1 (cellobiohydrolase 1) polypeptide derived from *Trichoderma*.

Thus, the present invention provides a polynucleotide comprising the codon-modified HRP polynucleotide to which a polynucleotide encoding a desired polypeptide is further added.

In the present invention, the desired polypeptide is not particularly limited. If the HRP polypeptide is added as a tag for detection, for example, the desired polypeptide can be easily detected.

On the other hand, in the present invention, the desired polypeptide may be added to the HRP polypeptide so as to purify the HRP polypeptide. An example of such a polypeptide used to purify the HRP polypeptide includes a polypeptide having a substrate adsorption ability. More specifically, the examples include cellobiohydrolase (CBH), endoglucanase, β-glucosidase, glucoamylase, albumin, antibodies, Fab antibodies, scFV antibodies, a His tag, a GST tag, an MBP tag, a TAP tag, a FLAG tag, a Myc tag, a HA tag, a V5 tag, and a T7 tag.

The codon-modified HRP polynucleotide and the polynucleotide encoding the desired polypeptide may be added in any mode, as long as a single string of a fusion polypeptide is translated without shifting reading frames of these polypeptides by the addition. The polynucleotide encoding the desired polypeptide may be added to either one or both of the 5' side and the 3' side of the codon-modified HRP polynucleotide. Moreover, such an addition may be direct or indirect. An example of the indirect addition includes a mode in which a polynucleotide encoding a linker polypeptide is inserted between the codon-modified HRP polynucleotide and the polynucleotide encoding the desired polypeptide. The length of such a linker polypeptide is normally 1 to 100 amino acids, preferably 1 to 50 amino acids, more preferably 1 to 30 amino acids, and particularly preferably 12 to 18 amino acids (for example, 15 amino acids).

<Expression Vector, Transformant>

The present invention also provides an expression vector comprising the polynucleotide of the present invention. The express ion vector of the present invention can be constructed based on a self-replicating vector, i.e., for example, a plasmid which exists as an extrachromosomal element, and which replicates independently of the replication of the chromosome. Alternatively, the expression vector of the present invention may be replicated together with the chromosome of a host filamentous fungus, after introduced into the filamentous fungus and incorporated into the genome thereof.

In order to express the HRP and the like after introduction into a filamentous fungus, the expression vector of the present invention desirably comprises, in addition to the polynucleotide of the present invention, a polynucleotide for regulating the expression, a gene marker for selecting the transformant, and the like.

Examples of such a polynucleotide for regulating the expression include a promoter, a leader sequence, a terminator, and the like. The promoter is not particularly limited, as long as the transcriptional activity is exhibited in the filamentous fungus. The promoter can be obtained as a polynucleotide for regulating an expression of a gene encoding any polypeptide of the same species or genus as that of a host filamentous fungus or any polypeptide of different species or genus. Examples of such a promoter include promoters of an α-amylase gene, a glucoamylase gene, a cellobiohydrolase gene, or a glyceraldehyde 3-phosphate dehydrogenase gene. The terminator should be a sequence recognized by a filamentous fungus to terminate the transcription. Examples thereof include terminators of TAKA amylase, a glucoamylase, a cellobiohydrolase gene, an anthranilate synthase, α-glucosidase, a trpC gene, or a trypsin-like protease gene. The leader sequence should be an untranslated region of an mRNA so that the translation efficiency by a filamentous fungus can be improved. Examples thereof include leader sequences of TAKA amylase, phosphotriose isomerase, or a glaA gene.

Further, the gene marker for selecting the transformant may be selected as appropriate in accordance with the method for selecting the transformant. For example, a gene encoding for drug resistance and a gene complementing the auxotrophy can be used. Examples of the gene marker include a uracil biosynthesis gene (pyr4), a nitrate assimilation gene (niaD), an arginine biosynthesis gene (argB), an acetamidase gene (amdS), an ornithine carbamoyltransferase gene (argB), a phosphinothricin acetyl transferase gene (bar), a phleomycin binding gene (bleA), a hygromycin phosphotransferase gene (hygB), an orotidine-5'-phosphate decarboxylase gene (pyrG), a sulfate adenyl transferase gene (sC), an anthranilate synthase gene (trpC), a destomycin resistance gene, a hygromycin resistance gene, a bialaphos resistance gene, a bleomycin resistance gene, and an aureobasidin resistance gene.

Those skilled in the art can design and prepare such a vector as appropriate by employing known genetic recombination techniques and the like.

Additionally, a HRP polypeptide and the like can be produced in a filamentous fungus by introducing such a vector of the present invent ion therein. Thus, the present invention provides a transformant of a filamentous fungus transformed with the expression vector introduced.

Examples of the filamentous fungus are as described above. Nevertheless, from the viewpoint that a HRP polypeptide and the like are produced in larger amounts, preferable are fungi belonging to the genus *Trichoderma* (particularly, *Trichoderma viride*) and fungi belonging to the genus *Aspergillus* (particularly, *Aspergillus niger*), more preferably fungi belonging to the genus *Trichoderma*, and particularly preferably *Trichoderma viride*.

The method for introducing the vector of the present invention is not particularly limited, and known methods can be employed. Examples of such known methods include a protoplast method, a calcium chloride method, an electroporation method, a competent method, a heat shock method, a spheroplast method, and a lithium acetate method. Furthermore, as described in Examples later, a so-called co-transformation method may be employed, in which the expression vector comprising the polynucleotide of the present invention and a vector comprising the gene marker are introduced at the same time.

<Method for Producing HRP Polypeptide and the Like, HRP Polypeptide and the Like, Preparation Comprising HRP Polypeptide and the Like>

The present invention makes it possible to produce a polypeptide encoded by the polynucleotide of the present invention, the production comprising:

culturing the transformant; and harvesting the HRP polypeptide and the like expressed from the cultured transformant and/or a culture of the transformant. In the present invention, the transformant can be cultured by selecting the medium, the culture condition, and the like as appropriate in accordance with a conventional method.

In the present invention, the "culture" refers to a medium obtained by culturing the transformant in a medium suitable for a filamentous fungus, the medium containing the proliferated transformant, a secretion and a metabolite of the transformant, and the like. The culture also includes a dilution and a concentrate of these.

It is only necessary that the media contain what a filamentous fungus can assimilate. Examples thereof include a carbon source, a nitrogen source, a sulfur source, minerals, metals, peptone, yeast extract, meat extract, casein hydrolysate, serum, and the like. Moreover, to such a medium, it is possible to add, for example, an antibiotic corresponding to a drug resistance gene which the expression vector of the present invention can encode, or a nutrient corresponding to the gene complementing the auxotrophy which the expression vector of the present invention can encode.

The culture condition according to the present invention should be a condition under which the transformant of the present invention can secrete and produce a HRP polypeptide and the like in the above-described medium. Those skilled in the art can adjust and set the temperature, whether to add air or not, oxygen concentration, carbon dioxide concentration, pH of the medium, culture temperature, culture period, humidity, and so forth as appropriate in accordance with the type of a filamentous fungus, the medium used, and the like.

Moreover, an example of the method for harvesting the HRP polypeptide and the like expressed from the cultured transformant includes a method in which: the transformant is collected (by filtration, centrifugation, or the like), the HRP polypeptide and the like are extracted (by grinding treatment, pressurization crushing, or the like) from the collected transformant, and further purified (by a salting-out method, a solvent precipitation method, or the like).

Further, the examples of the method for harvesting the HRP polypeptide and the like expressed from the transformant include a method in which the filamentous fungus is removed with a culture filter (for example, a filter having a pore size of 0.2 μm or less), and known methods such as extraction filtration, centrifugation, dialysis, concentration, drying, freezing, adsorption, desorption, methods utilizing a difference in solubility from various solutions (for example, precipitation, salting out, crystallization, recrystallization, transfer dissolution, chromatographies). Additionally, these methods may be employed alone, or may be employed in combination in any order or repeatedly.

Meanwhile, in the case where the polypeptide encoded by the polynucleotide of the present invention comprises a tag for purifying HRP as described above, the purification can be performed using a substrate to which the tag adsorbs.

By such a production method, the HRP polypeptide, the HRP polypeptide containing no signal sequence, or these polypeptides to which the desired polypeptide is added can be obtained. Thus, the present invention provides these HRP polypeptides and the like.

Meanwhile, since a HRP C1a polypeptide extracted from horseradish has a carbohydrate chain of approximately 10 kDa added thereto, such a HRP C1a polypeptide is detected as a polypeptide having a molecular weight of approximately 40 kDa in an analysis by SDS-PAGE or the like. On the other hand, as described in Examples later, a HRP C1a polypeptide obtained by the production method of the present invention is detected as a polypeptide having a molecular weight of approximately 32 kDa in an analysis by SDS- PAGE or the like. Further, although not described in Examples later, the present inventors have found that a carbohydrate chain of a HRP C1a polypeptide extracted from horseradish is not cleaved by glycosidase F; meanwhile, a carbohydrate chain of a HRP C1a polypeptide obtained by the production method of the present invention is cleaved by the enzyme. These findings have revealed that an α1,3-bound core fucose residue is added to a carbohydrate chain of a HRP C1a polypeptide extracted from horseradish, but no α1,3-bound core fucose residue is added to a carbohydrate chain of a HRP C1a polypeptide obtained by the production method of the present invention.

Thus, the HRP polypeptide and the like obtained by the production method of the present invention have a different carbohydrate chain modification from that of a HRP polypeptide produced in horseradish. Accordingly, the polypeptide of the present invention may be a polypeptide produced by the production method of the present invention and having a carbohydrate chain removed therefrom. The carbohydrate chain can be removed using an enzyme capable of breaking down and removing a carbohydrate chain. Examples of such an enzyme include glycosidase F (glycopeptidase F) and endoglycosidase H.

Furthermore, the present invention also provides a preparation comprising a HRP polypeptide and the like produced by the production method. The preparation of the present invention should comprise the HRP polypeptide and the like produced by the product ion method, but may comprise other ingredients acceptable as a preparation of the HRP polypeptide and the like, in addition to the HRP polypeptide and the like of the present invention. Examples of such other ingredients include a carrier, an excipient, a disintegrator, a buffer, an emulsifier, a suspension, a stabilizer, a preservative, an antiseptic, and a physiological salt. As the excipient, lactose, starch, sorbitol, D-mannitol, white sugar, or the like can be used. As the disintegrator, starch, carboxymethyl cellulose, calcium carbonate, or the like can be used. As the buffer, a phosphate, a citrate, an acetate, or the like can be used. As the emulsifier, gum arabic, sodium alginate, tragacanth, or the like can be used. As the suspension, glyceryl monostearate, aluminium monostearate, methyl cellulose, carboxymethyl cellulose, hydroxymethyl cellulose, sodium lauryl sulfate, or the like can be used. As the stabilizer, propylene glycol, diethylin sulfite, ascorbic acid, or the like can be used. As the preservative, phenol, benzalkonium chloride, benzyl alcohol, chlorobutanol, methylparaben, or the like can be used. As the antiseptic, sodium azide, benzalkonium chloride, para-hydroxybenzoic acid, chlorobutanol, or the like can be used.

<Use of HRP Polypeptide and the Like>

It is known that a HRP polypeptide acting as a catalyst oxidizes luminescent and chromogenic substrates such as luminol or TMB (tetramethylbenzidine), causing chemiluminescence and color development. Moreover, binding of a HRP polypeptide to a target molecule enables detection of the target molecule on the basis of the above chemiluminescence and the like. Thus, the present invention provides a method for detecting a target molecule, the method comprising binding of the target molecule to a polypeptide (the polypeptide of the present invention) produced by the product ion method of the present invention.

The target molecule detected by the method of the present invention is not particularly limited. Examples thereof include polypeptides, nucleic acids, sugars, and lipids.

In the method for detecting a target molecule of the present invention, the polypeptide of the present invention is bound to a target molecule. Accordingly, it is preferable that a molecule (for example, an antibody) capable of specifically binding to the target molecule be added to the polypeptide of the present invention. Moreover, it is also preferable to use the polypeptide of the present invention to which a molecule (so-called second antibody, protein A, or protein G which recognize an antibody that is the molecule concerned in case) capable of specifically binding to the molecule concerned is added.

Such an addition is not particularly limited, and may be an addition at a gene level, or may be a chemical addition. The addition at a gene level is accomplished by using a codon-modified HRP polynucleotide to which a polynucleotide encoding the antibody or the like is added as the polynucleotide of the present invention as described above. Moreover, the chemical addition may be a covalent bond, or may be a non-covalent bond. The "covalent bond" is not particularly limited, and examples thereof include an amide bond between an amino group and a carboxyl group, an alkylamine bond between an amino group and an alkyl halide group, a disulfide bond between thiols, and a thioester bond between a thiol group and a maleimide group or an alkyl halide group. An example of the "non-covalent bond" includes a binding between biotin and avidin.

Examples of the luminescent and chromogenic substrates used in the method for detecting a target molecule of the present invention include luminol, TMB, pyrogallol, guaiacol, and dianisidine.

Moreover, as described in Examples later, the polypeptide of the present invention is capable of discoloring a pigment such as annatto in the presence of hydrogen peroxide. Thus, the present invention provides a method for discoloring a pigment, the method comprising causing a polypeptide produced by the method of the present invention to act on the pigment in presence of hydrogen peroxide.

Examples of the pigment discolored by the method of the present invention include annatto, orange II, Alizarin Red S, Tropaeolin O, and chalcone. Further, those skilled in the art can set reaction conditions in such a pigment discoloration, that is, the concentration and temperature of hydrogen peroxide, the type and pH of a system (for example, a buffer) in which the HRP polypeptide and the pigment are mixed together, and so forth, as appropriate in accordance with the type and the like of the pigment subjected to the discoloration.

Additionally, a HRP polypeptide acting as a catalyst oxidizes a phenol moiety in a phenolic compound to a phenoxy radical. The phenoxy radical then forms a water insoluble multimer by polymerization by itself. Further, it is known that the multimer can be easily removed as a precipitate.

Thus, the present invention can also provide a method for removing a phenolic compound, the method comprising causing a polypeptide produced by the method of the present invention to act on the phenolic compound in presence of hydrogen peroxide.

The phenolic compound removed by the method of the present invention is not particularly limited, as long as the compound has a phenol moiety to be oxidized by a peroxidase as described above. Examples of the phenolic compound include p-cresol, p-ethyl phenol, and p-n-propyl phenol. Further, those skilled in the art can set reaction conditions in the removal of such a phenolic compound, that is, the concentration and temperature of hydrogen peroxide, the type and pH of a system (for example, a buffer) in which the HRP polypeptide and the phenolic compound are mixed together, and so forth, as appropriate in accordance with the type of the phenolic compound.

EXAMPLES

Hereinafter, the present invention will be more specifically described based on Examples and Comparative Example. However, the present invention is not limited to Examples below.

Comparative Example 1

Expression Examination of Wild-Type Horseradish Peroxidase (HRP) in Filamentous Fungus First, a filamentous fungus (*Trichoderma viride*) was transformed using a wild-type base sequence encoding a wild-type HRP polypeptide, and an expression of the HRP polypeptide in the resulting transformants was examined by the following method.

(1) Preparation of Wild-Type HRP C1a Gene

As the sequence of the wild-type HRP C1a gene, the base sequence (base sequence of SEQ ID NO: 3) described in "Eur. J. Biochem., 1988, vol. 173, iss. 3, pp. 681 to 687" was used to artificially synthesize the wild-type HRP gene. In the artificial synthesis, a recognition site of a restriction enzyme StuI and a recognition site of a restriction enzyme XhoI were added to the sequence respectively upstream of the initiation codon and downstream of the stop codon. Then, the resulting synthesized wild-type HRP gene was inserted in pMA-T having been treated with a restriction enzyme SfiI. Thus, a plasmid "pHRP_Native" was obtained.

(2) Construction of Wild-Type HRP Expression Plasmid "pCB1-HRP_Native"

The plasmid "pHRP_Native" was cleaved with StuI and XhoI to thus obtain approximately 1 kbp of a gene fragment "HRP_Native". On the other hand, a plasmid "pCB1-Eg3X-hphless" (see International Publication No. WO2011/021616) was cleaved with StuI and XhoI to collect approximately 6 kbp of a fragment. To this, "HRP_Native" was ligated using TaKaRa DNA Ligation Kit, Mighty Mix (manufactured by Takara Shuzo Co., Ltd.) to thus prepare a plasmid "pCB1-HRP_Native". The reaction conditions such as enzymes were in accordance with the conditions in the instruction attached to the kit. The sequence of the inserted DNA fragment cloned in the plasmid "pCB1-HRP_Native" was determined using BigDye® Terminator v3.1 Cycle Sequencing kit (manufactured by Applied Biosystems Inc.) and ABI PRISM® Genetic Analyzer (manufactured by Applied Biosystems Inc.) in accordance with the attached protocol. The plasmid "pCB1-HRP_Native" was constructed so as to express a HRP polypeptide in the host *Trichoderma viride* by using the own initiation codon.

(3) Preparation of *Trichoderma* vi ride Transformant by Plasmid "pCB1-HRP_Native"

*Trichoderma* vi ride was transformed with the plasmid "pCB1-HRP_Native" in accordance with the method described in International Publication No. WO2005/056787. The transformation was carried out by a co-transformation method using a *Trichoderma viride* strain 2 deficient for a uracil biosynthesis gene (pyr4) as a host and a pyr4 gene of *Neurospora crassa* as a selection marker. The *Trichoderma viride* strain 2 was cultured in 50 mL of a fungal cell-forming medium (1% yeast extract, 1% malt extract, 2% polypeptone, 2.5% glucose, 0.1% dipotassium hydrogen phosphate, 0.05% magnesium sulfate heptahydrate, 0.0001% uridine (pH 7.0)) at 28° C. for 24 hours, and centrifuged at 3000 rpm for 10 minutes to collect the fungal cells. The obtained fungal cells were washed with 0.5 mol/L of sucrose, and suspended in a protoplast-forming enzyme solution (1 mg/mL of β-glucuronidase, 0.3 mg/mL of chitinase, 0.3 mg/mL of zymolyase, 0.5 mol/L of sucrose) that had been filtered through cotton. The resultant was shaken at 30° C. for 60 minutes, so that the hypha was formed into a protoplast. This suspension was filtered and then centrifuged at 2500 rpm for 10 minutes to collect the protoplast, which was washed with a SUTC buffer (0.5 mol/L of sucrose, 10 mmol/L of calcium chloride, 10 mmol/L of Tris-HCl (pH 7.5)).

The protoplast was suspended in 100 μL of a SUTC buffer, and then 7 μL of a DNA solution containing 7 μg of the plasmid "pCB1-HRP_Native" and 3 μL of a DNA solution containing the pyr4 gene were added thereto. The mixture was left to stand in ice for 5 minutes. Next, 400 μL of a PEG solution (60% PEG4000, 10 mmol/L of calcium chloride, 10 mmol/L of Tris-HCl (pH 7.5)) was added thereto, and left to stand in ice for 20 minutes. Subsequently, 10 mL of a SUTC buffer was added thereto and centrifuged at 2500 rpm for 10 minutes. The protoplast thus collected was suspended in 1 mL of a SUTC buffer, and each 200 μL of the suspension was overlaid together with soft agar on a minimum medium containing 0.5 mol/L of sucrose, followed by culturing at 28° C. for 5 days. Thereafter, grown colonies were again transferred to a minimum medium. The colonies formed thereon were used as transformants.

(4) Culturing and Identification of Transformant by "pCB1-HRP_Native"

A strain which grew in the minimum medium after the introduction of the plasmid "pCB1-HRP_Native" was selected, and cultured at 28° C. in a P medium (1.0% glucose, 4.0% lactose, 2.0% soybean cake, 1.0% yeast extract, 0.5% potassium phosphate, 0.2% ammonium sulfate, 0.2% calcium carbonate, 0.03% magnesium sulfate), using a flask in accordance with the method described in International Publication No. WO98/11239 (WO 98-11239 A). Then, in order to check whether or not HRP was expressed, the resulting culture supernatant was separated by electrophoresis using 12% Gel SDS-PAGE mini (manufactured by TEFCO), and blotted on a PVDF membrane (manufactured by Millipore Corporation). Western blot using an anti-HRP antibody (manufactured by JIRL Co., product number: 123-055-021) was performed on the blotted PVDF membrane. FIG. 1 shows the obtained result.

As apparent from the result shown in FIG. 1, no HRP-derived band was detected by the western blot using the anti-HRP antibody from the culture supernatant of the transformant by pCB1-HRP_Native. Thus, it was revealed that no HRP was produced from such a transformant obtained by transforming a filamentous fungus using a polynucleotide having no different base sequence from the wild-type base sequence encoding a HRP polypeptide.

Example 1

Expression Examination of HRP Polypeptide in *Humicola* by HRP Polynucleotide Modified in Consideration of Codon Usage Frequencies of Three Filamentous Fungal Species in *Humicola*, *Aspergillus*, and *Trichoderma*

From the above result, in order to express a HRP polypeptide in a filamentous fungus at a high level, codon usage frequencies of three filamentous fungal species in *Humicola*, *Aspergillus*, and *Trichoderma* were taken into consideration. In order to improve the translation efficiency in all of these three species, a polynucleotide was prepared, which was modified to have a base sequence different from the base sequence of the wild-type HRP gene. Then, *Humicola* (*Humicola insolens*) was first transformed using this polynucleotide to examine an expression of a HRP polypeptide in the resulting transformant. Hereinafter, these methods and the obtained results will be described.

(1) Creation of Codon Table for Optimizing Expression in All Three Species in *Humicola, Aspergillus*, and *Trichoderma*

In order to improve the translation efficiency in all the three species in *Humicola, Aspergillus*, and *Trichoderma*, a codon usage frequency table shown in Table 1 was created in consideration of codon usage frequencies of polypeptides whose expression was observed in the three species. Specifically, in the fungi of the three species, if a codon usage frequency was extremely low (if the usage frequency is less than 5%) even in one species of the fungi, the usage frequency was set to "00". Moreover, as to a codon having a usage frequency of 5% or more in all the fungi of the three species, an average of the usage frequencies of the three or two species of the fungi was calculated, and the average was altered to a multiple of 5. In this manner, the codon usage frequency table shown in Table 1 was created.

TABLE 1

| | | SECOND LETTER | | | | |
|---|---|---|---|---|---|---|
| | | .T. | .C. | .A. | .G. | |
| FIRST | T.. | Phe 0 | Ser 0 | Tyr 0 | Cys 0 | ..T   THIRD |
| LETTER | T.. | Phe 100 | Ser 85 | Tyr 100 | Cys 100 | ..C   LETTER |
| | T.. | Leu 0 | Ser 0 | Stop 0 | Stop 0 | ..A |
| | T.. | Leu 0 | Ser 0 | Stop 100 | Trp 100 | ..G |
| | C.. | Leu 0 | Pro 20 | His 0 | Arg 10 | ..T |
| | C.. | Leu 80 | Pro 80 | His 100 | Arg 90 | ..C |
| | C.. | Leu 0 | Pro 0 | Gln 0 | Arg 0 | ..A |
| | C.. | Leu 20 | Pro 0 | Gln 100 | Arg 0 | ..G |
| | A.. | Ile 0 | Thr 0 | Asn 0 | Ser 0 | ..T |
| | A.. | Ile 100 | Thr 85 | Asn 100 | Ser 15 | ..C |
| | A.. | Ile 0 | Thr 0 | Lys 0 | Arg 0 | ..A |
| | A.. | Met 100 | Thr 15 | Lys 100 | Arg 0 | ..G |
| | G.. | Val 10 | Ala 20 | Asp 5 | Gly 25 | ..T |
| | G.. | Val 85 | Ala 80 | Asp 95 | Gly 75 | ..C |
| | G.. | Val 0 | Ala 0 | Glu 0 | Gly 0 | ..A |
| | G.. | Val 5 | Ala 0 | Glu 100 | Gly 0 | ..G |

(2) Preparation of Codon-Modified HRP Polynucleotide for Optimizing Express ion in All Three Species in *Humicola, Aspergillus*, and *Trichoderma*

In order to express the HRP gene as an active polypeptide at a high level in the three species in *Humicola, Aspergillus*, and *Trichoderma*, a HRP polynucleotide was modified. Specifically, on the basis of the codon usage frequencies shown in Table 1, the base sequence of SEQ ID NO: 1 was designed from the base sequence of the wild-type HRP gene (base sequence of SEQ ID NO: 3) with 28.5% of bases being altered (see FIGS. 2 and 3). Note that, in the base sequence of the modified HRP polynucleotide thus designed, 246 codons among all 338 codons were altered; in other words, 72.8% of all the codons were modified (degeneracy mutation). Next, on the basis of information on this base sequence, a modified HRP polynucleotide was artificially synthesized and inserted in pMA-T, similarly to pHRP_Native, to thus obtain a plasmid "pHRP" in which the codon-modified HRP polynucleotide was inserted.

(3) Construction of Codon-Modified HRP Polynucleotide Expression Plasmid "pNCE2-HRP-*humicola*" for *Humicola*

On the basis of the base sequence of the codon-modified HRP polynucleotide, the following primers were further designed and prepared so as to express a His tag added to the C-terminal side of a polypeptide to be encoded by the polynucleotide.

HRP-humicola-F:
(SEQ ID NO: 5)
CCCGGATCCTGGGACAAGATGCACTTCTCCAGCTCCTCC

HRP-humicola-R:
(SEQ ID NO: 6)
CCCGGATCCCTAGTGATGGTGATGATGGTGGTGGTGGGAGTTGGAGTTG
ACGACG.

Then, using these primers and "pHRP" as a template, PCR was carried out. The PCR was performed using PrimeSTAR@ Max DNA Polymerase (manufactured by Takara Bio Inc.). The PCR was performed in 30 cycles each consisting of "98° C. for 10 seconds, 55° C. for 5 seconds, and 72° C. for 10 seconds." Approximately 1 kbp of a DNA fragment thus amplified was cleaved with BamHI to thus obtain approximately 1 kbp of a gene fragment "HRP-*humicola*". On the other hand, a plasmid "pJND-c5" (see International Publication No. WO01/090375 (WO 01-090375 A)) was cleaved with BamHI to collect approximately 8 kbp of a fragment. To this, HRP-*humicola* was ligated using TaKaRa DNA Ligation Kit, Mighty Mix to thus prepare a plasmid "pNCE2-HRP-*humicola*". The sequence of the inserted DNA fragment cloned in the plasmid "pNCE2-HRP-*humicola*" was analyzed by the method described in Comparative Example 1 (2). The plasmid "pNCE2-HRP-*humicola*" was constructed so as to express a HRP polypeptide in the host *Humicola insolens* by using the own initiation codon.

(4) Preparation of *Humicola insolens* Transformant by Plasmid "pNCE2-HRP-*Humicola*"

*Humicola insolens* was transformed with the plasmid "pNCE2-HRP-*humicola*" in accordance with the method described in WO 01-090375 A. The transformation was carried out using a *Humicola insolens* strain MN200-1 as a host and hygromycin as a selection marker. The *Humicola insolens* strain MN200-1 was cultured in an (S) medium at 37° C. After 24 hours, the fungal cells were collected by centrifugation at 3000 rpm for 10 minutes. The composition of the (S) medium was: 3.0% glucose, 2.0% yeast extract, 0.1% peptone, 0.03% calcium chloride, and 0.03% magnesium chloride, with pH 6.8. The obtained fungal cells were washed with 0.5 M sucrose, and suspended in 10 ml of a protoplast-forming enzyme solution (3 mg/ml of β-glucuronidase, 1 mg/ml of chitinase, 1 mg/ml of zymolyase, 0.5 M sucrose) that had been filtered through a 0.45-μm filter. The resultant was shaken at 30° C. for 60 to 90 minutes, so that the hypha was formed into a protoplast. This suspension was filtered and then centrifuged at 2500 rpm for 10 minutes to collect the protoplast, which was washed with a SUTC buffer (0.5 M sucrose, 10 mM calcium chloride, 10 mM Tris-HCl (pH 7.5)).

The protoplast was suspended in 1 mL of a SUTC buffer, and 10 μg of the plasmid "pNCE2-HRP-*humicola*" was added thereto. The mixture was left to stand in ice for 5 minutes. Next, 400 μL of a PEG solution (60% PEG4000, 10 mM calcium chloride, 10 mM Tris-HCl (pH 7.5)) was added thereto, and left to stand in ice for 20 minutes. Subsequently, 10 mL of a SUTC buffer was added thereto and centrifuged at 2500 rpm for 10 minutes. The protoplast thus collected was suspended in 1 mL of a SUTC buffer, then centrifuged at 4000 rpm for 5 minutes, and finally suspended in 100 μL of a SUTC buffer. The protoplast having been treated as described above was overlaid together with soft agar on a hygromycin (200 μg/mL)-supplemented regeneration YMG medium (1% glucose, 0.4% yeast extract, 0.2% malt extract, 17.8% raffinose, 1% agar, pH 6.8), followed by culturing at 37° C. for 5 days. Thereafter, grown colonies were again transferred to a hygromycin (200 μg/mL)-supplemented regeneration YMG medium. The colonies grown thereon were used as transformants.

(5) Culturing and Identification of Transformant by "pNCE2-HRP-*Humicola*"

Figure 4:
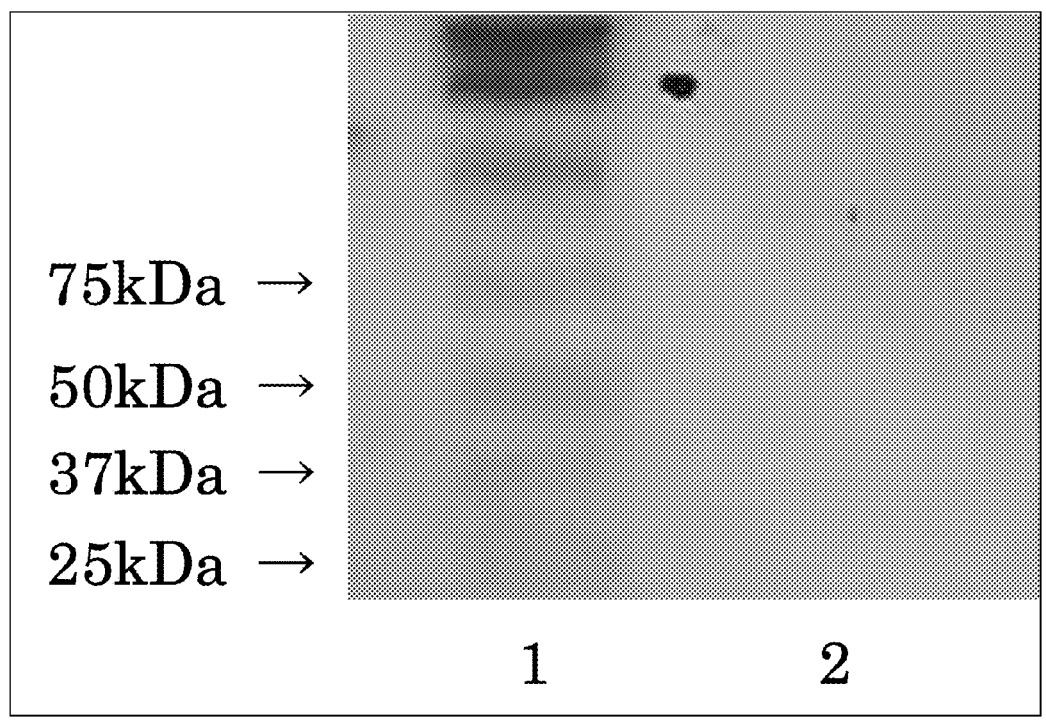
FIG. 4 is a photograph for illustrating the result of transforming *Humicola* with an expression vector (pNCE2-HRP-*humicola*) comprising the polynucleotide of the present invention, and analyzing a culture supernatant of the resulting transformant by the western blot using an anti-His tag antibody. In the figure, lane 1 shows the result of spreading a molecular weight marker, and lane 2 shows the result of spreading the culture supernatant of the transformant.

A strain which grew in the hygromycin-supplemented regeneration YMG medium after the introduction of the plasmid "pNCE2-HRP-*humicola*" was selected, and cultured in accordance with the method described in WO 01-090375 A. Then, in order to check whether or not HRP was expressed, the resulting culture supernatant was separated by electrophoresis using 12% Gel SDS-PAGE mini, and blotted on a PVDF membrane (manufactured by Millipore Corporation). Western blot using an anti-His tag antibody (manufactured by MBL Co., Ltd., product number: D291-7) was performed on the blotted PVDF membrane. FIG. 4 shows the obtained result.

As apparent from the result shown in FIG. 4, no HRP-derived band was detected by the western blot using the anti-His tag antibody from the culture supernatant of the transformant by pNCE2-HRP-*humicola*. Thus, it was revealed that no HRP was produced from such a transformant obtained by transforming *Humicola* using a polynucleotide (codon-modified HRP polynucleotide) modified in consideration of the codon usage frequencies of the three filamentous fungal species in *Humicola, Aspergillus,* and *Trichoderma*.

Example 2

Expression Examination of HRP Polypeptide in *Aspergillus* by HRP Polynucleotide Modified in Consideration of Codon Usage Frequencies of Three Filamentous Fungal Species in *Humicola, Aspergillus,* and *Trichoderma*

Next, *Aspergillus* (*Aspergillus niger*) was transformed using the above-described codon-modified HRP polynucleotide to examine an expression of a HRP polypeptide in the resulting transformant.

Note that *Aspergillus* was transformed using an *Aspergillus niger* strain pyr1 deficient for a uracil biosynthesis gene (pyr4) as a host and a pyr4 gene derived from *Trichoderma viride* as a selection marker by the method described below.

(1) Construction of Expression Vector for *Aspergillus niger*

(1-1) Construction of *Trichoderma viride* Pyr4 Expression Plasmid "pUC-Pyr4" for Selection Marker First of all, the *Trichoderma viride* pyr4 gene used as the selection marker in the transformation of *Aspergillus niger* was cloned by the following method.

(1-1-1) Preparation of Genomic DNA Library of *Trichoderma viride*

From fungal cells of *Trichoderma viride*, the genomic DNA was isolated and purified according to the method of Horiuchi et al. (see H. Horiuchi et al., J. Bacteriol. 1988, vol. 170, pp. 272 to 278). The isolated genomic DNA was partially digested with a restriction enzyme Sau3AI. This was ligated to the BamHI arm of a phage vector, λEMBL3 cloning kit (manufactured by Stratagene Corporation) using Ligation Kit Ver. 2 (manufactured by Takara Shuzo Co., Ltd.). After ethanol precipitation, the resultant was dissolved in a TE buffer. All of the ligated mixture was used to form phage particles with a MaxPlax λ packaging kit (manufactured by Epicentre Technologies Co.) for the infection of an *Escherichia coli* strain XL1-blue MRA (P2). By this method, the genomic DNA library was obtained with $1.1 \times 10^4$ phages.

(1-1-2) Preparation of *Trichoderma viride* Pyr4 Probe

The following primers were prepared on the basis of a disclosed sequence of the translated region of *Trichoderma reesei*.

PYRMET:
(SEQ ID NO: 7)
ATGGCACCACACCCGACG

PYRSTOP:
(SEQ ID NO: 8)
CTATCGCAGTAGCCGCTC.

Using these primers and the genomic DNA isolated and purified above as a template, PCR was carried out. The PCR was performed using LA Taq Polymerase (manufactured by Takara Bio Inc.). The PCR was performed by a program executed in 30 cycles each consisting of "94° C. for 30 seconds, annealing for 30 seconds, and 72° C. for 2 minutes." Approximately 1100 bp of a DNA fragment thus amplified was inserted in a pCR2.1-TOPO plasmid vector using TOPO TA cloning kit (manufactured by Invitrogen Corporation) in accordance with the attached protocol. Thus, a plasmid "TOPO-PYR" was obtained.

The sequence of the inserted DNA fragment cloned in the plasmid "TOPO-PYR" was analyzed by the method described in Comparative Example 1 (2). Homology search was conducted on the base sequence thus obtained. As a result, the base sequence showed a homology with the *Trichoderma* PYR4 gene. Accordingly, it was determined that this DNA fragment was a portion of the PYR4 gene. The DNA fragment was amplified by the same PCR method as above using the plasmid "TOPO-PYR" as a template. The obtained PCR product was labelled using ECL Direct System (manufactured by Amersham Pharmacia Biotech Inc.) and used as a probe.

(1-1-3) Screening by Plaque Hybridization

Phage plaques formed above were transferred to a Hybond-N+ nylon transfer membrane (manufactured by Amersham plc), and alkali-treated with 0.4 N sodium hydroxide to denature the recombinant phage DNA on the membrane into single strands. After washed with 5×SSC (1×SSC: 15 mM trisodium citrate, 150 mM sodium chloride), the resultant was air-dried to fix the DNA. After that, the probe prepared above was used for hybridization according to the manual of the kit, followed by the detection reaction. The sensitization was effected on a FUJI medical X-ray film (manufactured by Fujifilm Corporation). Two positive clones were thus obtained. DNA was prepared from the positive clones according to the method of Maniatis et al. (J. Sambrook, E. F. Fritsch, and T. Maniatis, Molecular Cloning, Cold Spring Harbor Laboratory Press, 1989). The phage DNA was collected using LE392 as a host *Escherichia coli*. The phage DNA prepared as described above was treated with PstI, and the hybridization was carried out using the probe. As a result, approximately 0.8 kbp of a band was detected from phage clone 1, and approximately 2.2 kbp of a band was detected from phage clone 2.

(1-1-4) Construction of *Trichoderma viride* Pyr4 Expression Plasmid "pUC-Pyr4"

Approximately 0.8 kbp of the PstI fragment of phage clone 1 and approximately 2.2 kbp of the PstI fragment of phage clone 2 were cloned in pUC118, and plasmids "pUC-PYR-clone1" and "pUC-PYR-clone2" were obtained, respectively. The base sequences of the obtained plasmids were analyzed by the method described in Examples 1 and 2. The result revealed that "pUC-PYR-clone1" contained the terminator side of the Pyr4 gene while "pUC-PYR-clone2" contained the promoter side. "pUC-PYR-clone1" and "pUC-PYR-clone2" were treated with PstI, and subcloned in a ligated state in pUC118. Thus, a plasmid "pUC-Pyr4" was obtained.

(1-2) Construction of Expression Vector "pAmyB-pyr" for *Aspergillus niger*

In order to add an XbaI site to the plasmid "pUC-Pyr4", PCR was carried out using Tricho-pyr-N-xba and Tricho-pyr-C-xba as primers and "pUC-Pyr4" as a template. Approximately 2.5 kbp of a DNA fragment thus amplified was cleaved with XbaI. Thus, approximately 2.5 kbp of a gene fragment "Pyr4-xbaI" was obtained.

```
Tricho-pyr-N-xba:
                                    (SEQ ID NO: 9)
GGTCTAGACTGCAGGCACTTCCAGGCA Tricho-pyr-C-xba:
                                    (SEQ ID NO: 10)
GGTCTAGAGCATGACGAATACATATCAAAC.
```

On the other hand, a plasmid "pAMY" (see International Publication No. WO97/000944) was cleaved with XbaI to collect approximately 8.3 kbp of a fragment. To this, Pyr4-xbaI was ligated using TaKaRa DNA Ligation Kit, Mighty Mix to thus prepare a plasmid "pAMY-Pyr4". In order to add an EcoRV site to the plasmid "pAMY-Pyr4", PCR was carried out using amyB-P-R5R and amyB-T-R5R as primers and "pAMY-Pyr4" as a template. Thus, an expression vector "pAmyB-pyr" for *Aspergillus niger* was obtained, which contained the *Trichoderma viride* pyr4 gene.

```
amyB-P-R5R:
                                    (SEQ ID NO: 11)
GATATCTGTGGGGTTTATTGTTCAGAGAA amyB-T-R5R:
                                    (SEQ ID NO: 12)
GATATCAGGGTGGAGAGTATATGATGGTA.
```

(2) Construction of Codon-Modified HRP Expression Plasmid "pAmyB-pyr-HRP-*Aspergillus*" for *Aspergillus*

Next, the codon-modified HRP gene was inserted in the plasmid "pAmyB-pyr" constructed above. Specifically, first, on the basis of the base sequence of the codon-modified HRP gene, the following primers were further designed and prepared so as to express a His tag added to the C-terminal side of a polypeptide to be encoded by the polynucleotide.

```
HRP-Aspergillus-F:
                                    (SEQ ID NO: 13)
GGCATTTATGCACTTCTCCAGCTCCTCCA HRP-Aspergillus-R:
                                    (SEQ ID NO: 14)
CTAGTGATGGTGATGATGGTGGTGGTGGGAGTTGGAGTTGACGACG.
```

Then, using these primer and pHRP as a template, PCR was carried out. The PCR was performed using Prime-STAR® Max DNA Polymerase. Approximately 1 kbp of a DNA fragment thus amplified was phosphorylated to thus obtain approximately 1 kbp of a gene fragment "HRP-*Aspergillus*". On the other hand, the plasmid "pAmyB-pyr" prepared in Example 2 (1-2) was cleaved with EcoRV to collect approximately 8.9 kbp of a fragment. To this, approximately 1 kbp of the gene fragment "HRP-*Aspergillus*" was ligated using TaKaRa DNA Ligation Kit, Mighty Mix to thus prepare a plasmid "pAmyB-pyr-HRP-*Aspergillus*". The sequence of the inserted DNA fragment cloned in the plasmid "pAmyB-pyr-HRP-*Aspergillus*" was analyzed by the method described in Comparative Example 1 (2). The plasmid "pAmyB-pyr-HRP-*Aspergillus*" was constructed so as to express HRP in the host *Aspergillus niger* by using the own initiation codon.

(3) Creation of *Aspergillus niger* Strain Pyr1

Next, an *Aspergillus niger* strain pyr1 deficient for a uracil biosynthesis gene (pyr4) was created by the method described below.

Approximately $10^9$ CFU/mL of a spore suspension of an *Aspergillus niger* strain NRRL337 was irradiated with UV2 light at a height of 30 cm, while being gently mixed. This was applied to a selective medium and cultured at 30° C. for 7 days. A grown strain was selected, and thus an *Aspergillus niger* strain pyr1 was obtained. This selective medium had been prepared by adding 10 µg/mL of uridine and 4 mg/mL of 5-fluoroorotic acid to a minimum medium.

(4) Preparation of *Aspergillus niger* Transformant by Plasmid "pAmyB-pyr-HRP-*Aspergillus*"

Transformation was carried out using an *Aspergillus niger* strain pyr1 deficient for pyr4 as a host and the pyr4 gene as a selection marker.

Specifically, first, the *Aspergillus niger* strain pyr1 was cultured in an (s) medium at 30° C. After 24 hours, the fungal cells were collect by centrifugation at 3000 rpm for 10 minutes. The composition of the (S) medium was: 3.0% glucose, 2.0% yeast extract, 0.1% peptone, 0.03% calcium chloride, and 0.03% magnesium chloride, with pH 6.8. The obtained fungal cells were washed with 4% sodium chloride, and suspended in 10 ml of a protoplast-forming enzyme solution (3 mg/ml of β-glucuronidase, 1 mg/ml of chitinase, 1 mg/ml of zymolyase, 4% sodium chloride) that had been filtered through a 0.45-µm filter. The resultant was shaken at 30° C. for 60 to 90 minutes, so that the hypha was formed into a protoplast. This suspension was filtered and then centrifuged at 2500 rpm for 10 minutes to collect the protoplast, which was washed with a SUTC buffer (0.5 M sucrose, 10 mM calcium chloride, 10 mM Tris-HCl (pH 7.5)).

The protoplast was suspended in 1 mL of a SUTC buffer, and 10 µg of the plasmid "pAmyB-pyr-HRP-*Aspergillus*" was added thereto. The mixture was left to stand in ice for 5 minutes. Next, 400 µL of a PEG solution (60% PEG4000, 10 mM calcium chloride, 10 mM Tris-HCl (pH 7.5)) was added thereto, and left to stand in ice for 20 minutes. Subsequently, 10 ml of a SUTC buffer was added thereto and centrifuged at 2500 rpm for 10 minutes. The protoplast thus collected was suspended in 1 mL of a SUTC buffer, then centrifuged at 4000 rpm for 5 minutes, and finally suspended in 100 µL of a SUTC buffer. Each 200 µL of the protoplast having been treated as described above was overlaid together with soft agar on a minimum medium containing 0.5 mol/L of sucrose, followed by culturing at 30° C. for 5 days. Thereafter, grown colonies were again transferred to a minimum medium. The colonies formed thereon were used as transformants.

(5) Culturing and Identification of Transformant by "pAmyB-pyr-HRP-*Aspergillus*"

Figure 5:
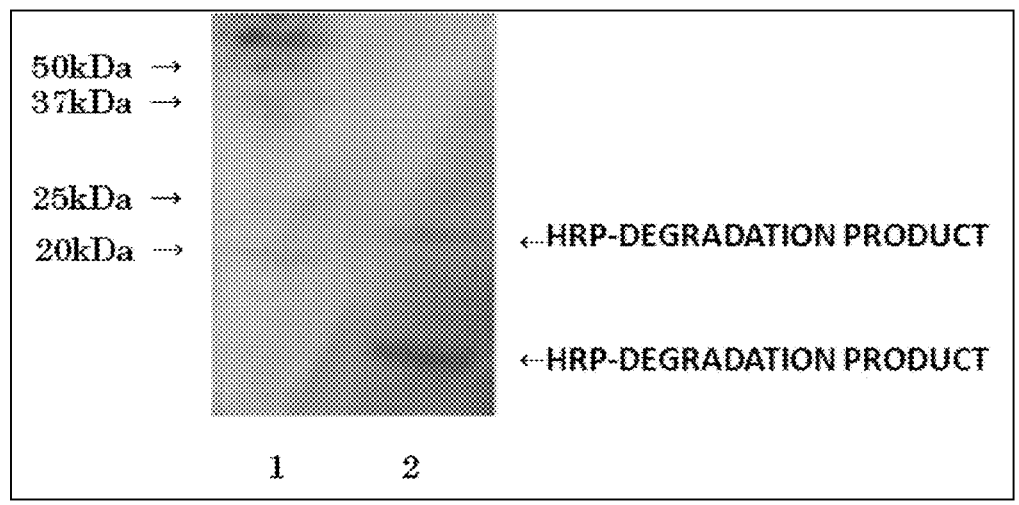
FIG. 5 is a photograph for illustrating the result of transforming *Aspergillus* with an expression vector (pAmyB-pyr-HRP-*Aspergillus*) comprising the polynucleotide of the present invention, and analyzing a culture supernatant of the resulting transformant by the western blot using the anti-His tag antibody. In the figure, lane 1 shows the result of spreading a molecular weight marker, and lane 2 shows the result of spreading the culture supernatant of the transformant.

A strain which grew in the minimum regeneration medium after the introduction of the plasmid "pAmyB-pyr-HRP-*Aspergillus*" was selected, inoculated into a production medium, and cultured at 30° C. for 4 days. The resulting culture supernatant was separated by electrophoresis using 12% Gel SDS-PAGE mini, and blotted on a PVDF membrane (manufactured by Millipore Corporation). Western blot using the anti-His tag antibody was performed on the blotted PVDF membrane. FIG. 5 shows the obtained result.

As apparent from the result shown in FIG. 5, HRP-derived bands (HRP breakdown products of approximately 24 kDa, 22 kDa, and 15 kDa) were detected by the western blot using the anti-His tag antibody from the culture supernatant of the transformant by pAmyB-pyr-HRP-*Aspergillus*. Thus, it was revealed that in the case where *Aspergillus* was transformed using a polynucleotide (codon-modified HRP polynucleotide) modified in consideration of the codon usage frequencies of the three filamentous fungal species in *Humicola*, *Aspergillus*, and *Trichoderma*, a HRP polypeptide was produced from such a transformant.

(6) Measurement of HRP Concentration in Culture Supernatant of Transformant by pAmyB-pyr-HRP-*Aspergillus*

The culture supernatant of the transformant by pAmyB-pyr-HRP-*Aspergillus* was diluted as appropriate. A tetramethylbenzidine reagent (manufactured by Cosmo Bio Co., Ltd.) was added to the culture supernatant diluted in such a manner that the concentration of the transformant was $9 \times 10^8$ CFU/mL. The mixture was left to stand at room temperature for 10 minutes. After the react ion was stopped by adding 1 N sulfuric acid thereto, the absorbance at a wavelength of 450 nm was measured to calculate the amount of HRP. Note that, for the calibration curve, a HRP reagent (Wako: 169-10791) manufactured by Wako Pure Chemical Industries, Ltd. was used, which had been diluted to approximately 0.625 to 10 ng/mL with Milli Q water. As a result, the HRP concentration in the culture supernatant of the transformant by pAmyB-pyr-HRP-*Aspergillus* was 0.004 mg/L.

Example 3

Expression Examination of HRP Polypeptide in *Trichoderma* by HRP Polynucleotide Modified in Consideration of Codon Usage Frequencies of Three Filamentous Fungal Species in *Humicola, Aspergillus*, and *Trichoderma*

Next, *Trichoderma* (*Trichoderma viride*) was transformed using the above-described codon-modified HRP polynucleotide to examine an expression of a HRP polypeptide in the resulting transformant.

(1) Construction of Codon-Modified HRP Polynucleotide Expression Plasmids "pCB1-HRP-Tricho" and "pCB1-HRP(Hisless)-Tricho"

On the basis of the base sequence of the codon-modified HRP polynucleotide, the following primers were prepared.

```
HRP-tricho-F:
                                        (SEQ ID NO: 15)
GGGAGGCCTGCGCATCATGCACTTCTCCAG HRP-tricho-R:
                                        (SEQ ID NO: 16)
CCCCTCGAGCTAGGAGTTGGAGTTGACGAC HRP-tricho-R(Hisless):
                                        (SEQ ID NO: 17)
CCCCTCGAGCTAGGAGTTGGAGTTGACGAC.
```

Using HRP-tricho-F and HRP-tricho-R or HRP-tricho-F and HRP-tricho-R(Hisless) as a primer set and pHRP as a template, PCR was carried out. The PCR was performed using PrimeSTAR® Max DNA Polymerase. Approximately 1 kbp of a DNA fragment thus amplified was cleaved with StuI and XhoI to thus obtain approximately 1 kbp of each of gene fragments "HRP-N" and "HRP-N(Hisless)". On the other hand, a plasmid "pCB1-Eg3X-hphless" was cleaved with StuI and XhoI to collect approximately 6 kbp of a fragment. To this, one of HRP-N and HRP-N(Hisless) was ligated using TaKaRa DNA Ligation Kit, Mighty Mix to prepare plasmids "pCB1-HRP-tricho" and "pCB1-HRP(Hisless)-tricho". The sequences of the inserted DNA fragments cloned in the plasmids "pCB1-HRP-tricho" and "pCB1-HRP(Hisless)-tricho" were analyzed by the method described in Comparative Example 1 (2). The plasmids "pCB1-HRP-tricho" and "pCB1-HRP(Hisless)-tricho" were each constructed so as to express HRP in the host *Trichoderma viride* by using the own initiation codon.

(2) Preparation of *Trichoderma viride* Transformant by Plasmid "pCB1-HRP-Tricho" or "pCB1-HRP(Hisless)-Tricho"

*Trichoderma viride* was transformed with the plasmid "pCB1-HRP-tricho" or "pCB1-HRP(Hisless)-tricho" by the method described in Comparative Example 1 (3).

(3) Culturing and Identification of Transformant by "pCB1-HRP-Tricho" or "pCB1-HRP(Hisless)-Tricho"

Figure 6:
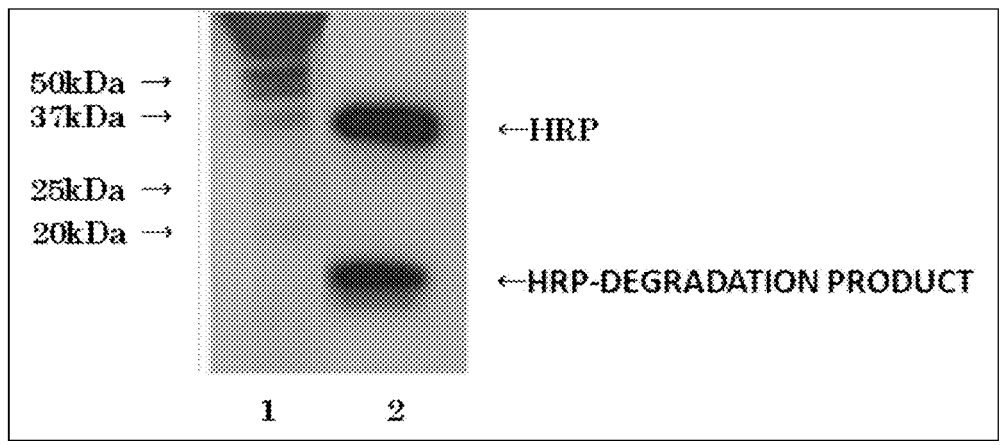
FIG. 6 is a photograph for illustrating the result of transforming *Trichoderma* with an expression vector (pCB1-HRP-tricho comprising the polynucleotide of the present invention, and analyzing a culture supernatant of the resulting transformant by the western blot using the anti-His tag antibody. In the figure, lane 1 shows the result of spreading a molecular weight marker, and lane 2 shows the result of spreading the culture supernatant of the transformant.
Figure 7:
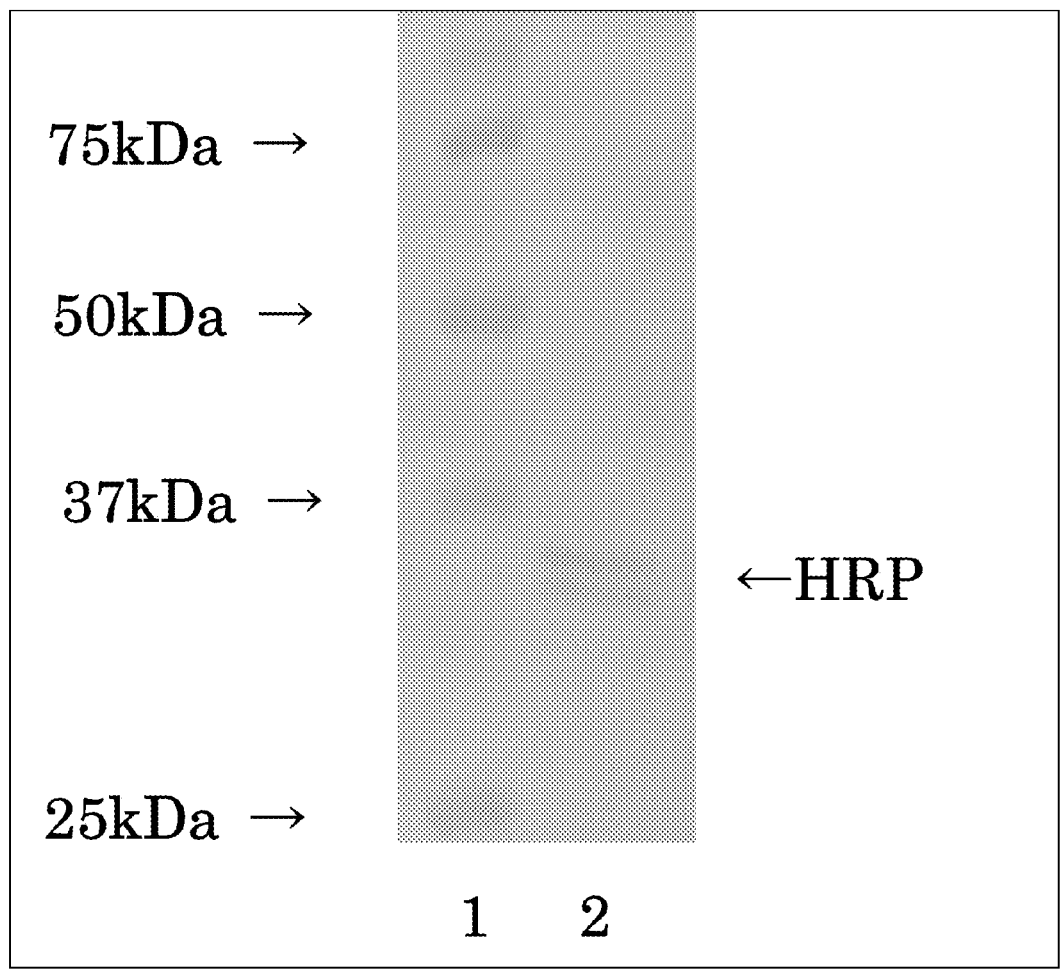
FIG. 7 is a photograph for illustrating the result of transforming *Trichoderma* with an expression vector (pCB1-HRP(Hisless)-tricho) comprising the polynucleotide of the present invention, and analyzing a culture supernatant of the resulting transformant by the western blot using the anti-HRP antibody. In the figure, lane 1 shows the result of spreading a molecular weight marker, and lane 2 shows the result of spreading the culture supernatant of the transformant.

A strain which grew in the minimum medium after the introduction of one of the plasmids "pCB1-HRP-tricho" and "pCB1-HRP(Hisless)-tricho" was selected, and cultured at 28° C. in the P medium, using a flask or a jar fermentor in accordance with the method described in WO 98-11239 A. In order to check whether or not HRP was expressed, the resulting culture supernatant was separated by electrophoresis using 12% Gel SDS-PAGE mini, and blotted on a PVDF membrane (manufactured by Millipore Corporation). Western blot using the anti-His tag antibody was performed on the blotted PVDF membrane in the case of pCB1-HRP-tricho, while western blot using the anti-HRP antibody was performed in the case of pCB1-HRP(Hisless)-tricho. FIGS. 6 and 7 show the obtained results.

As apparent from the results shown in FIGS. 6 and 7, a HRP-derived band (HRP of approximately 32 kDa) was detected from both of the culture supernatant of the transformant by pCB1-HRP-tricho and the culture supernatant of the transformant by pCB1-HRP(Hisless)-tricho. Thus, it was revealed that in the case where *Trichoderma* was transformed using a polynucleotide (codon-modified HRP polynucleotide) modified in consideration of the codon usage frequencies of the three filamentous fungal species in *Humicola, Aspergillus*, and *Trichoderma*, a HRP polypeptide was produced from such a transformant.

(4) Measurement of HRP Concentration and Guaiacol Oxidation Activity in Culture Supernatant of Transformant by "pCB1-HRP-Tricho" or "pCB1-HRP(Hisless)-Tricho"

The culture supernatant in the flask culturing of the transformant by "pCB1-HRP-tricho" or "pCB1-HRP(Hisless)-tricho" was diluted as appropriate in such a manner that the concentration of the transformant was $9 \times 10^8$ CFU/mL. The HRP concentration was measured in accordance with Example 2 (6). As a result, the HRP concentration in the culture supernatant of the transformant by pCB1-HRP-tricho was 123 mg/L, while the HRP concentration in the culture supernatant of the transformant by pCB1-HRP(Hisless)-tricho was 165 mg/L. Similarly, the culture supernatant in the jar fermentor culturing of the transformant by "pCB1-HRP-tricho" or "pCB1-HRP(Hisless)-tricho" was diluted as appropriate in such a manner that the concentration of the transformant was $9 \times 10^8$ CFU/mL. The HRP concentration was measured in accordance with Example 2 (6). As a result, the HRP concentration in the culture supernatant of the transformant by pCB1-HRP-tricho was 317 mg/L, while the HRP concentration in the culture supernatant of the transformant by pCB1-HRP(Hisless)-tricho was 525 mg/L.

Further, the guaiacol oxidation activity was measured using the culture supernatant in the flask culturing of the transformant by "pCB1-HRP-tricho" or "pCB1-HRP(Hisless)-tricho". Specifically, 0.05 mL of the culture supernatant diluted as appropriate with a phosphate buffer (pH 7.0) was added to 3.05 mL of a 0.1-M phosphate buffer (pH 7.0) containing 1 µmol of guaiacol and 0.3 µmol of hydrogen peroxide. The change in the absorbance was measured at a wavelength of 436 nm for 10 to 15 minutes in the reaction. Note that the guaiacol oxidation activity is defined as an activity of oxidizing 1 µmol of guaiacol in one minute, and is expressed as an activity per mg of a polypeptide contained in a culture supernatant (U/mg protein). As a result, the guaiacol oxidation activity in the culture supernatant of the transformant by pCB1-HRP-tricho was 1.54 U/mg protein, while the guaiacol oxidation activity in the culture supernatant of the transformant by pCB1-HRP(Hisless)-tricho was 7.60 U/mg protein. Similarly, using the culture supernatant in the jar fermentor culturing of the transformant by "pCB1-HRP-tricho" or "pCB1-HRP(Hisless)-tricho", the guaiacol oxidation activity was measured. As a result, the guaiacol oxidation activity in the culture supernatant of the transformant by pCB1-HRP-tricho was 3.95 U/mg protein, while the guaiacol oxidation activity in the culture supernatant of the transformant by pCB1-HRP(Hisless)-tricho was 5.49 U/mg protein.

Example 4

Expression Examination of Fusion Polypeptide Between HRP and *Trichoderma* CBH1 Utilizing Codon-Modified HRP Polynucleotide in *Trichoderma*

Whether or not it was possible to express a fusion polypeptide between HRP and another polypeptide in a filamentous fungus at a high level by using the above-described codon-modified HRP polynucleotide was examined by the method described below.

(1) Construction of CBH1 Co-Expression Vector "pCB1-KR" for *Trichoderma viride*

In order to delete a CBH1 cellulase binding site of a plasmid "pCB1-Eg3X-hphless" and to insert a HpaI site and a PstI site therein, PCR was carried out using TrichoCBH1HpaR and aTrichoPstF as primers and pCB1-Eg3X-hphless as a template. Thus, a CBH1 co-expression vector "pCB1-KR" was obtained.

```
TrichoCBH1HpaR:
                                    (SEQ ID NO: 18)
GGTTAACCTGAGTAGGGCCGGGAGAGGA aTrichoPstF:
                                    (SEQ ID NO: 19)
GGCTGCAGTAAGGTACTCGAGCAAAAGCTT.
```

(2) Construction of Plasmid "pCB1-KR-HRP-tricho" for Expressing Fusion Polypeptide Between HRP and CBH1

On the basis of the base sequence of the codon-modified HRP polynucleotide, the following primers were prepared.

```
HRPHpaKR:
                                    (SEQ ID NO: 20)
GCTATTGAGAAGCGCCAGCTCACCCCTACCTTCTACGAC

PERAspglaC:
                                    (SEQ ID NO: 21)
CTAGGAGTTGGAGTTGACGAC.
```

Using these primers and pHRP as a template, PCR was carried out. The PCR was performed using PrimeSTAR® Max DNA Polymerase. Approximately 1 kbp of a DNA fragment thus amplified was phosphorylated to thus obtain approximately 1 kbp of a gene fragment "HRP-Hpa". On the other hand, the plasmid "pCB1-KR" was cleaved with HpaI to collect approximately 6 kbp of a fragment. To this, HRP-Hpa was ligated using TaKaRa DNA Ligation Kit, Mighty Mix to thus prepare a plasmid "pCB1-KR-HRP-tricho". The sequence of the inserted DNA fragment cloned in the plasmid "pCB1-KR-HRP-tricho" was analyzed by the method described in Comparative Example 1 (2). The plasmid "pCB1-KR-HRP-tricho" was constructed so as to express as a fusion polypeptide between CBH1 and HRP in the host *Trichoderma viride*.

(3) Preparation of *Trichoderma viride* Transformant by Plasmid "pCB1-KR-HRP-Tricho"

*Trichoderma viride* was transformed with the plasmid "pCB1-KR-HRP-tricho" by the method described in Comparative Example 1 (3).

(4) Culturing and Identification of Transformant by pCB1-KR-HRP-Tricho

Figure 8:
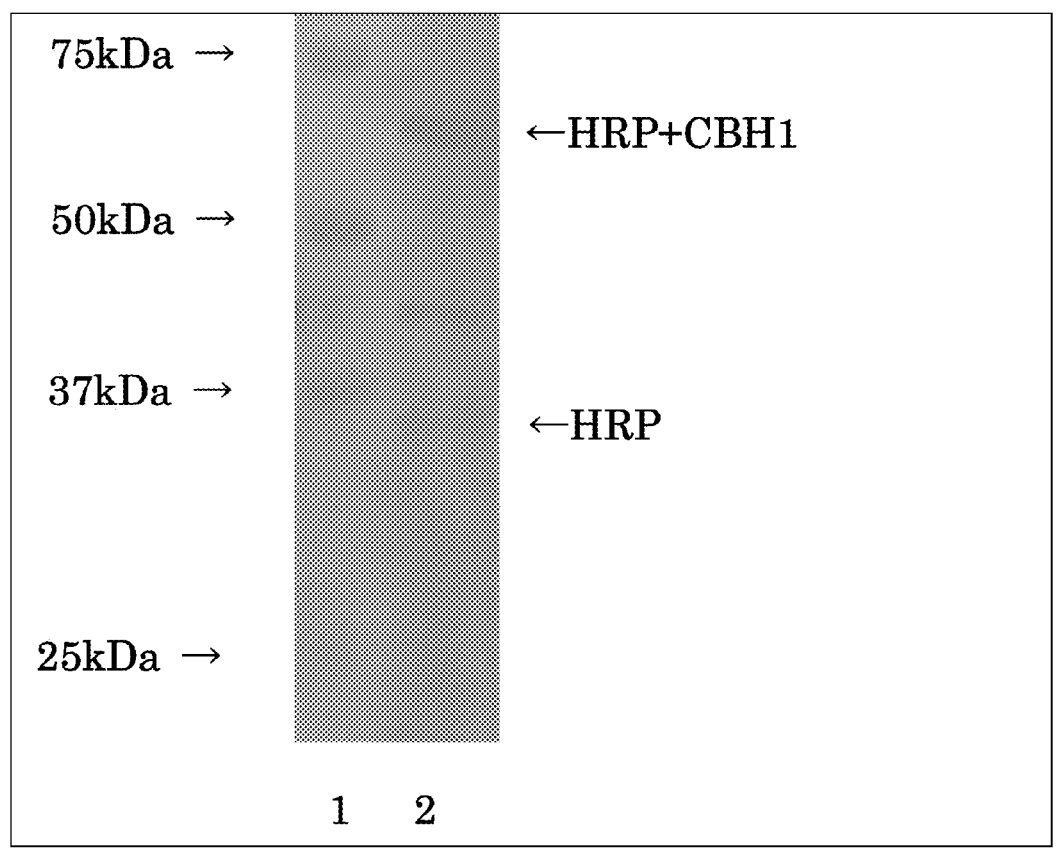
FIG. 8 is a photograph for illustrating the result of transforming *Trichoderma* with an expression vector (pCB1-KR-HRP-tricho) comprising the polynucleotide of the present invention, and analyzing a culture supernatant of the resulting transformant by the western blot using the anti-HRP antibody. In the figure, lane 1 shows the result of spreading a molecular weight marker, and lane 2 shows the result of spreading the culture supernatant of the transformant.

A strain which grew in the minimum medium after the introduction of the plasmid "pCB1-KR-HRP-tricho" was selected, and cultured at 28° C. in the P medium, using a flask in accordance with the method described in WO 98-11239 A. In order to check whether or not HRP was expressed, the resulting culture supernatant was separated by electrophoresis using 12% Gel SDS-PAGE mini, and blotted on a PVDF membrane (manufactured by Millipore Corporation). Western blot using the anti-HRP antibody was performed on the blotted PVDF membrane. FIG. 8 shows the obtained result.

As apparent from the result shown in FIG. 8, a band of approximately 70 kDa, that is, the fusion polypeptide between CBH1 and HRP was detected from the culture supernatant of the transformant by pCB1-KR-HRP-tricho. Thus, it was revealed that in the case where *Trichoderma* was transformed using a polynucleotide (codon-modified HRP polynucleotide) modified in consideration of the codon usage frequencies of the three filamentous fungal species in *Humicola, Aspergillus*, and *Trichoderma*, a fusion polypeptide comprising HRP was produced from such a transformant.

(5) Measurement of HRP Concentration in Culture Supernatant of Transformant by pCB1-KR-HRP-Tricho The transformant by pCB1-KR-HRP-tricho was cultured at 28° C. in the P medium, using a flask in accordance with the method described in WO 98-11239 A. Then, the resulting culture supernatant was diluted as appropriate in such a manner that the concentration of the transformant was $9 \times 10^8$ CFU/mL. The HRP concentration was measured in accordance with Example 2 (6). The HRP concentration in the culture supernatant of the transformant by pCB1-KR-HRP-tricho was 123 mg/L.

Example 5

Purification Examination Using Fusion Polypeptide Between HRP and his Tag Utilizing Codon-Modified HRP Polynucleotide (1) Purification by HisTrap HP Column Two ml of the culture supernatant of the transformant by pCB1-HRP-tricho which was cultured in Example 3 (3) was supplied to a HisTrap HP column (manufactured by GE) equilibrated with 0.02 M $Na_2HPO_4$ and 0.5 M NaCl (pH 7.5) buffer. After the column was washed with the buffer used for the equilibration, the resultant was eluted with 0.02 M $Na_2HPO_4$, 0.5 M NaCl, and 0.5 M imidazole (pH 7.5) buffer.

The concentration of HRP contained in the eluate was measured in accordance with Example 2 (6). As a result, HRP at a concentration of 103.9 ng/ml was collected.

Example 6

Purification Examination Using Fusion Polypeptide Between HRP and Trichoderma CBH1 Utilizing Codon-Modified HRP Polynucleotide (1) Purification Utilizing Binding Activity to Avicel Ten μl of the culture supernatant of the transformant by pCB1-KR-HRP-tricho which was cultured in Example 4 (4) was mixed well with 90 μl of an Avicel solution at 2% concentration (20 mM acetic acid buffer (pH 5.0), 1 M ammonium sulfate), and left to stand at 25° C. for 10 minutes. After centrifugation, the supernatant was removed, and 20 mM acetic acid buffer (pH 5.0) and 1 M ammonium sulfate were added to the resultant, followed by washing with an Avicel solution (performed twice). After the final centrifugation, the supernatant was removed, and the resultant was mixed with Milli Q water, left at 37° C. for 10 minutes, and separated from Avicel. After the separation, the supernatant was collected. The concentration of HRP contained in the supernatant was measured in accordance with Example 2 (6). As a result, HRP at a concentration of 12.7 ng/ml was collected.

Example 7

Annatto Pigment Degradation Test on Horseradish Peroxidase Recombinant Polypeptide Expressed in Trichoderma An annatto pigment degradation was measured using the culture supernatant of the transformant by pCB1-HRP-tricho which was cultured in Example 3 (3). After 10 μL of the culture supernatant was added to 190 μL of a 0.1 M phosphate buffer (pH 6.0) containing 1 μmol of an annatto pigment (manufactured by Wako Pure Chemical Industries, Ltd.) and 0.14 μmol of hydrogen peroxide, the mixture was left to stand at 37° C. for an appropriate period. Then, the change in the absorbance at 454 nm was measured. As a result, a decrease in the absorbance was detected after 30 minutes from the reaction, revealing that HRP expressed from the codon-modified HRP gene described above showed an annatto pigment degradation activity.

Example 8

Expression Examination of HRP Polypeptide in Trichoderma by HRP Polynucleotide Adapted Only for Codon Usage Frequencies of Trichoderma From the above results, in order to express a HRP polypeptide at a higher level in Trichoderma which had showed the highest HRP production ability among the three filamentous fungal species, a HRP polynucleotide was prepared, which was modified to have a base sequence adapted for the usage frequencies of Trichoderma. Then, Trichoderma was transformed using this polynucleotide to examine an expression of a HRP polypeptide in the resulting transformant. Hereinafter, the method and the obtained result will be described.

(1) Creation of Codon Table for Optimizing Expression in Trichoderma

A codon usage frequency table shown in Table 2 was created in consideration of codon usage frequencies of polypeptide whose expression was observed in Trichoderma (Trichoderma viride).

TABLE 2

| FIRST LETTER | SECOND LETTER | | | | THIRD LETTER |
|---|---|---|---|---|---|
| | .T. | .C. | .A. | .G. | |
| T.. | Phe 0 | Ser 7.5 | Tyr 0 | Cys 0 | ..T |
| T.. | Phe 100 | Ser 7.5 | Tyr 100 | Cys 100 | ..C |
| T.. | Leu 0 | Ser 0 | Stop 0 | Stop 0 | ..A |
| T.. | Leu 0 | Ser 0 | Stop 100 | Trp 100 | ..G |
| C.. | Leu 0 | Pro 20 | His 0 | Arg 0 | ..T |
| C.. | Leu 90 | Pro 80 | His 100 | Arg 100 | ..C |
| C.. | Leu 0 | Pro 0 | Gln 0 | Arg 0 | ..A |
| C.. | Leu 10 | Pro 0 | Gln 100 | Arg 0 | ..G |
| A.. | Ile 0 | Thr 5 | Asn 0 | Ser 0 | ..T |
| A.. | Ile 100 | Thr 95 | Asn 100 | Ser 85 | ..C |
| A.. | Ile 0 | Thr 0 | Lys 0 | Arg 0 | ..A |
| A.. | Met 100 | Thr 0 | Lys 100 | Arg 0 | ..G |
| G.. | Val 5 | Ala 10 | Asp 10 | Gly 5 | ..T |
| G.. | Val 95 | Ala 90 | Asp 90 | Gly 95 | ..C |
| G.. | Val 0 | Ala 0 | Glu 0 | Gly 0 | ..A |
| G.. | Val 0 | Ala 0 | Glu 100 | Gly 0 | ..G |

(2) Preparation of Codon-Modified HRP Polynucleotide for Optimizing Expression in Trichoderma In order to express the HRP gene as an active protein at a high level in Trichoderma (Trichoderma viride), a HRP polynucleotide was modified. Specifically, on the basis of the codon usage frequencies shown in Table 2, a base sequence of SEQ ID NO: 22 was designed from the base sequence of the wild-type HRP gene (base sequence of SEQ ID NO: 3) with 29.9% of bases being altered. Note that, in the base sequence of the modified HRP polynucleotide thus designed, 242 codons among all the 338 codons were altered; in other words, 71.6% of all the codons were modified (degeneracy mutation). Next, on the basis of information on this base sequence, a modified HRP polynucleotide was artificially synthesized and inserted in pMA-T, similarly to pHRP_Native, to thus obtain a plasmid "pHRP-2" in which the codon-modified HRP polynucleotide was inserted.

(3) Construction of Codon-Modified HRP Polynucleotide Expression Plasmid "pCB1-HRP(Hisless)-Tricho-2"

On the basis of the base sequence of the codon-modified HRP polynucleotide, the following primers were prepared. HRP-tricho-2-F: GGGAGGCCTGCGCATCATGCACT-TCA (SEQ ID NO: 24) HRP-tricho-2-R(Hisless): CCCGTCGACGCTGTTGCTGTTGACGACGCGGCA-GTT (SEQ ID NO: 25).

Using HRP-tricho-2-F and HRP-tricho-2-R(Hisless) as a primer set and pHRP-2 as a template, PCR was carried out. The PCR was performed using PrimeSTAR® Max DNA Polymerase. Approximately 1 kbp of a DNA fragment thus amplified was cleaved with StuI and SalI to thus obtain approximately 1 kbp of a gene fragment "HRP-N(Hisless)-

2". On the other hand, a plasmid "pCB1-Eg3X-hphless" was cleaved with StuI and XhoI to collect approximately 6 kbp of a fragment. To this, HRP-N(Hisless)-2 was ligated using TaKaRa DNA Ligation Kit, Mighty Mix to thus prepare a plasmid "pCB1-HRP(Hisless)-tricho-2". The sequence of the inserted DNA fragment cloned in the plasmid "pCB1-HRP(Hisless)-tricho-2" was analyzed by the method described in Comparative Example 1 (2). The plasmid "pCB1-HRP(Hisless)-tricho-2" was constructed so as to express HRP in the host Trichoderma viride by using the own initiation codon.

(4) Preparation of Trichoderma Transformant by Plasmid "pCB1-HRP(Hisless)-Tricho-2"

Trichoderma (Trichoderma viride) was transformed with the plasmid "pCB1-HRP(Hisless)-tricho-2" by the method described in Comparative Example 1 (3).

(5) Culturing and Identification of Transformant by "pCB1-HRP(Hisless)-Tricho-2"

Figure 9:
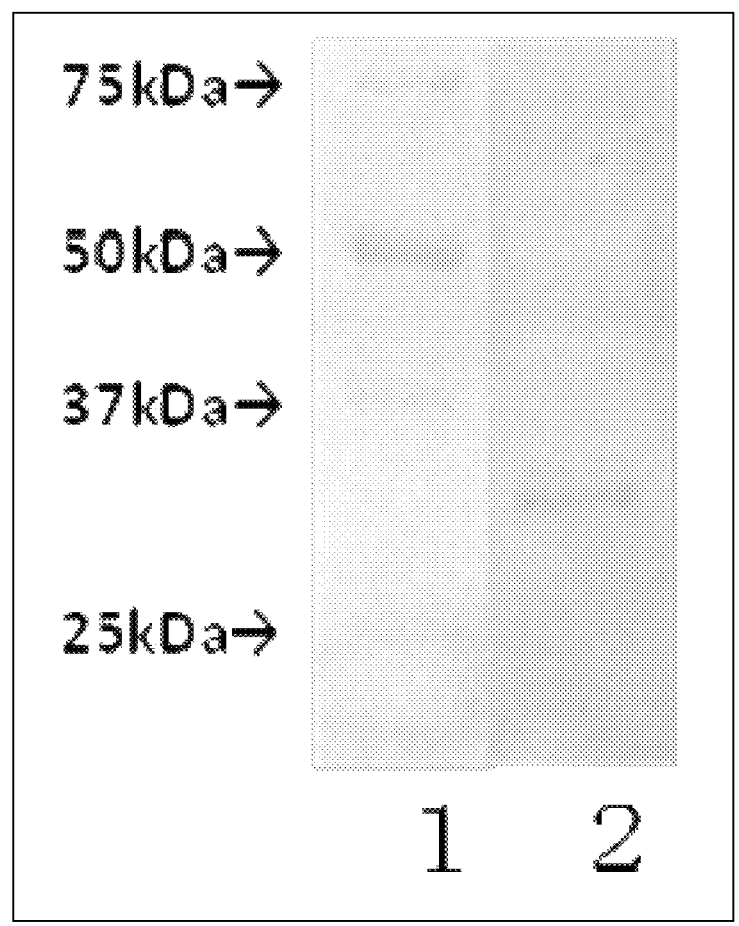
FIG. 9 is a photograph for illustrating the result of transforming *Trichoderma* with an expression vector (pCB1-HRP(Hisless)-tricho-2) comprising a HRP polynucleotide adapted only for codon usage frequencies of *Trichoderma*, and analyzing a culture supernatant of the resulting transformant by the western blot using the anti-HRP antibody. In the figure, lane 1 shows the result of spreading a molecular weight marker, and lane 2 shows the result of spreading the culture supernatant of the transformant.

A strain which grew in the minimum medium after the introduction of the plasmid "pCB1-HRP(Hisless)-tricho-2" was selected, and cultured at 28° C. in the P medium, using a flask in accordance with the method described in WO 98-11239 A. In order to check whether or not HRP was expressed, the resulting culture supernatant was separated by electrophoresis using 12% Gel SDS-PAGE mini, and blotted on a PVDF membrane (manufactured by Millipore Corporation). Western blot using the anti-HRP antibody was performed on the blotted PVDF membrane. FIG. 9 shows the obtained result.

(6) Measurement of HRP Concentration in Culture Supernatant of Transformant by "pCB1-HRP(Hisless)-Tricho-2"

The culture supernatant in the flask culturing of the transformant by "pCB1-HRP(Hisless)-tricho" was diluted as appropriate in such a manner that the concentration of the transformant was $9 \times 10^8$ CFU/mL. The HRP concentration was measured in accordance with Example (6).

As apparent from the result shown in FIG. 9, a HRP1-derived band (HRP of approximately 32 kDa) was detected from the culture supernatant of the transformant by pCB1-HRP(Hisless)-tricho-2. However, the HRP concentration in the culture supernatant in the flask culturing of the transformant by pCB1-HRP(Hisless)-tricho-2 was 24 mg/L and significantly low in comparison with that of the transformant by "pCB1-HRP(Hisless)-tricho" (165 mg/L, see Example 3).

Thus, it was revealed that a HRP polypeptide was produced in a larger amount in the case where Trichoderma was transformed using the polynucleotide modified in consideration of the codon usage frequencies of the three filamentous fungal species in Humicola, Aspergillus, and Trichoderma than the case where Trichoderma was transformed using the polynucleotide adapted only for the codon usage frequencies of Trichoderma.

Example 9

Expression Examination (2) of HRP Polypeptide in Trichoderma by HRP Polynucleotide Modified in Consideration of Codon Usage Frequencies of Three Filamentous Fungal Species in Humicola, Aspergillus, and Trichoderma From the above results, in order to check the effectiveness of the base sequence designed in consideration of the codon usage frequencies of the three filamentous fungal species in Humicola, Aspergillus, and Trichoderma, a polynucleotide was prepared, which was modified in consideration of the codon usage frequencies of the three filamentous fungal species and had a different sequence from that of the codon-modified HRP polynucleotide described in Examples 1 to 3. Then, Trichoderma was transformed using the polynucleotide to examine an expression of a HRP polypeptide in the resulting transformant. Hereinafter, the method and the obtained result will be described.

(1) Preparation of HRP Polynucleotide Modified in Consideration of Codon Usage Frequencies of Three Filamentous Fungal Species in Humicola, Aspergillus, and Trichoderma In order to express the HRP gene as an active protein at a high level in Trichoderma, a HRP polynucleotide was modified. Specifically, on the basis of the codon usage frequencies shown in Table 1, the base sequence of SEQ ID NO: 26 was designed from the base sequence of the wild-type HRP gene (base sequence of SEQ ID NO: 3) with 28.0% of bases being altered.

Note that, in the base sequence of the modified HRP polynucleotide thus designed, 245 codons among all the 338 codons were altered; in other words, 72.5% of all the codons were modified (degeneracy mutation) (see FIGS. 10 and 11). In addition, the number of bases different was ten between the base sequence of the modified HRP polynucleotide designed in this Example (1017 bases) and the base sequence of the codon-modified HRP polynucleotide described in Examples 1 to 3 (1017 bases), and the homology was 99% (see FIGS. 12 and 13).

Next, on the basis of information on this base sequence, a modified HRP polynucleotide was artificially synthesized and inserted in pMA-T, similarly to pHRP_Native, to thus obtain a plasmid "pHRP-3" in which the codon-modified HRP polynucleotide was inserted.

(2) Construction of Codon-Modified HRP Polynucleotide Expression Plasmid "pCB1-HRP(Hisless)-Tricho-3"

The plasmids "pHRP-3" and "pCB1-Eg3X-hphless" were cleaved with StuI and XhoI to collect approximately 1 kbp and approximately 6 kbp of fragments. The two were ligated using TaKaRa DNA Ligation Kit, Mighty Mix to prepare a plasmid "pCB1-HRP(Hisless)-tricho-3". The sequence of the inserted DNA fragment cloned in the plasmid "pCB1-HRP(Hisless)-tricho-3" was analyzed by the method described in Comparative Example 1 (2). The plasmid "pCB1-HRP(Hisless)-tricho-3" was constructed so as to express HRP in the host Trichoderma viride by using the own initiation codon.

(4) Preparation of Trichoderma Transformant by Plasmid "pCB1-HRP(Hisless)-Tricho-3"

Trichoderma (Trichoderma viride) was transformed with the plasmid "pCB1-HRP(Hisless)-tricho-3" by the method described in Comparative Example 1 (3).

(5) Culturing and Identification of Transformant by "pCB1-HRP(Hisless)-Tricho-3"

Figure 14:
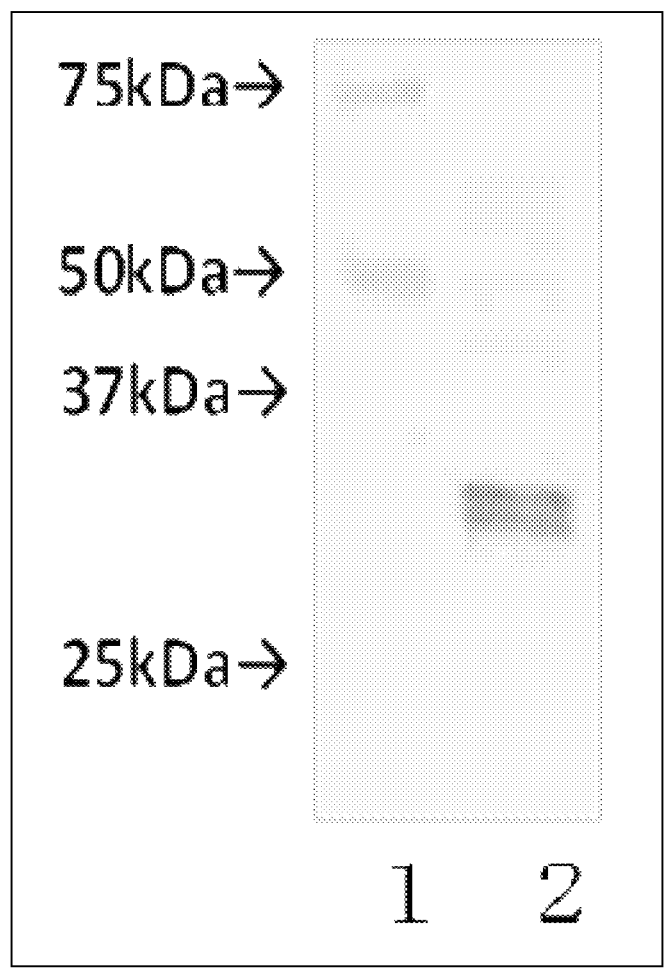
FIG. 14 is a photograph for illustrating the result of transforming *Trichoderma* with an expression vector (pCB1-HRP(Hisless)-tricho-3) comprising the polynucleotide of the present invention, and analyzing a culture supernatant of the resulting transformant by the western blot using the anti-HRP antibody. In the figure, lane 1 shows the result of spreading a molecular weight marker, and lane 2 shows the result of spreading the culture supernatant of the transformant.

A strain which grew in the minimum medium after the introduction of the plasmid "pCB1-HRP(Hisless)-tricho-3" was selected, and cultured at 28° C. in the P medium, using a flask in accordance with the method described in WO 98-11239 A. In order to check whether or not HRP was expressed, the resulting culture supernatant was separated by electrophoresis using 12% Gel SDS-PAGE mini, and blotted on a PVDF membrane (manufactured by Millipore Corporation). Western blot using the anti-HRP antibody was performed on the blotted PVDF membrane. FIG. 14 shows the obtained result.

As apparent from the result shown in FIG. 14, a HRP-derived band (HRP of approximately 32 kDa) was detected from the culture supernatant of the transformant by pCB1-HRP(Hisless)-tricho-3.

(6) Measurement of HRP Concentration in Culture Supernatant of Transformant by "pCB1-HRP(Hisless)-Tricho-3"

The transformant by "pCB1-HRP(Hisless)-tricho-3" was cultured at 28° C. in the P medium, using a flask in accordance with the method described in WO 98-11239 A. Then, the culture supernatant was diluted as appropriate in such a manner that the concentration of the transformant was $9\times10^8$ CFU/mL. The HRP concentration was measured in accordance with Example 2 (6). As a result, the HRP concentration in the culture supernatant of the transformant by pCB1-HRP(Hisless)-tricho-3 was 200 mg/L.

Thus, it was confirmed, similarly to Examples 2 to 5, that in the case where a filamentous fungus was transformed using a polynucleotide modified in consideration of the codon usage frequencies of the three filamentous fungal species in *Humicola*, *Aspergillus*, and *Trichoderma*, a HRP polypeptide was produced from such a transformant.

INDUSTRIAL APPLICABILITY

As described hereinabove, the present invent ion makes it possible to efficiently produce a large amount of a horseradish peroxidase polypeptide by introducing into a filamentous fungus a polynucleotide modified to have codon(s) whose base sequence is different from a wild-type base sequence encoding a horseradish peroxidase (HRP) polypeptide. The usage frequency of the modified codon(s) corresponds to the codon usage frequencies of the three filamentous fungal species in *Humicola*, *Aspergillus*, and *Trichoderma*.

Therefore, the polynucleotide and the method for producing a HRP polypeptide using the polynucleotide of the present invention are excellent in efficiently producing a large amount of a uniform HRP isozyme, and accordingly are useful in producing enzymes for detection, enzymes for clinical inspection kits, and the like in various tests such as enzyme-linked immunosorbent assay, immunohistostaining method, Southern blotting method, and western blotting method.

[Sequence Listing Free Text]
SEQ ID NOs: 1 and 26
<223> Artificially synthesized polynucleotide sequences in which the codon usage frequencies are adapted for *Trichoderma*, *Humicola*, and *Aspergillus*
SEQ ID NO: 2
<223> Polypeptide encoded by the artificially synthesized polynucleotide having the base sequence of SEQ ID NO: 1
SEQ ID NOs: 5 to 21, 24, and 25
<223> Artificially synthesized primer sequences
SEQ ID NO: 22
<223> Artificially synthesized polynucleotide sequence in which the codon usage frequencies are adapted for *Trichoderma*
SEQ ID NO: 23
<223> Polypeptide encoded by the artificially synthesized polynucleotide having the base sequence of SEQ ID NO: 22
SEQ ID NO: 27
<223> Polypeptide encoded by the artificially synthesized polynucleotide having the base sequence of SEQ ID NO: 26

The invention claimed is:

1. A polynucleotide modified to have at least one codon whose base sequence is different from a wild-type base sequence encoding a horseradish peroxidase polypeptide, having codon usage frequencies in the following percentages, and being capable of expressing the polypeptide to be encoded in a filamentous fungus, wherein
in a case where an amino acid encoded by the modified codon is alanine, a usage frequency of GCC is 80% and a usage frequency of GCT is 20%;
in a case where the amino acid encoded by the modified codon is arginine, a usage frequency of CGC is 90% and a usage frequency of CGT is 10%;
in a case where the amino acid encoded by the modified codon is asparagine, a usage frequency of AAC is 100%;
in a case where the amino acid encoded by the modified codon is aspartic acid, a usage frequency of GAC is 95% and a usage frequency of GAT is 5%;
in a case where the amino acid encoded by the modified codon is cysteine, a usage frequency of TGC is 100%;
in a case where the amino acid encoded by the modified codon is glutamine, a usage frequency of CAG is 100%;
in a case where the amino acid encoded by the modified codon is glutamic acid, a usage frequency of GAG is 100%;
in a case where the amino acid encoded by the modified codon is glycine, a usage frequency of GGC is 75% and a usage frequency of GGT is 25%;
in a case where the amino acid encoded by the modified codon is histidine, a usage frequency of CAC is 100%;
in a case where the amino acid encoded by the modified codon is isoleucine, a usage frequency of ATC is 100%;
in a case where the amino acid encoded by the modified codon is leucine, a usage frequency of CTC is 80% and a usage frequency of CTG is 20%;
in a case where the amino acid encoded by the modified codon is lysine, a usage frequency of AAG is 100%;
in a case where the amino acid encoded by the modified codon is phenylalanine, a usage frequency of TTC is 100%;
in a case where the amino acid encoded by the modified codon is proline, a usage frequency of CCC is 80% and a usage frequency of CCT is 20%;
in a case where the amino acid encoded by the modified codon is serine, a usage frequency of AGC is 15% and a usage frequency of TCC is 85%;
in a case where the amino acid encoded by the modified codon is threonine, a usage frequency of ACC is 85% and a usage frequency of ACG is 15%;
in a case where the amino acid encoded by the modified codon is tyrosine, a usage frequency of TAC is 100%; and
in a case where the amino acid encoded by the modified codon is valine, a usage frequency of GTC is 85%, a usage frequency of GTG is 5%, and a usage frequency of GTT is 10% wherein said polynucleotide encodes a horseradish peroxidase C1a polypeptide and has at least one characteristic selected from the group consisting of the following (i) to (iv):
(i) comprising a coding region of a base sequence of SEQ ID NO: 1;
(ii) having a sequence identity of 95% or more with a base sequence at positions 91 to 1017 of SEQ ID NO: 1;
(iii) comprising a coding region of a base sequence of SEQ ID NO: 26; and
(iv) having a sequence identity of 95% or more with a base sequence at positions 91 to 1017 of SEQ ID NO: 26.

2. The polynucleotide according to claim 1, wherein at least two codons are modified.

3. The polynucleotide according to claim 1, wherein at least 10% of codons are modified.

4. A polynucleotide comprising the polynucleotide according to claim 1, to which a polynucleotide encoding a desired polypeptide is added.

5. An expression vector comprising the polynucleotide according to claim 1.

6. A transformant of a filamentous fungus transformed with the expression vector according to claim 5 introduced.

7. The transformant according to claim 6, wherein the filamentous fungus is any one of a fungus belonging to genus *Trichoderma* and a fungus belonging to genus *Aspergillus*.

8. The transformant according to claim 6, wherein the filamentous fungus is any one of *Trichoderma viride* and *Aspergillus niger*.

9. The transformant according to claim 6, wherein filamentous fungus is *Trichoderma viride*.

10. A method for producing a polypeptide encoded by the polynucleotide according to claim 1, the method comprising the steps of:
  culturing the transformant of a filamentous fungus transformed with an expression vector comprising the polynucleotide according to claim 1; and
  harvesting the polypeptide expressed from the cultured transformant and/or a culture of the transformant.

* * * * *

SEQUENCE LISTING

```
<160> NUMBER OF SEQ ID NOS: 27

<210> SEQ ID NO 1
<211> LENGTH: 1017
<212> TYPE: DNA
<213> ORGANISM: Artificial Sequence
<220> FEATURE:
<223> OTHER INFORMATION: Synthetic polynucleotide sequence in which
      codon usage was adapted for Trichoderma, Humicola and Aspergillus
<220> FEATURE:
<221> NAME/KEY: CDS
<222> LOCATION: (1)..(1017)

<400> SEQUENCE: 1 atg cac ttc tcc agc tcc tcc acc ctc ttc acg tgc atc acc ctc atc        48
Met His Phe Ser Ser Ser Thr Leu Phe Thr Cys Ile Thr Leu Ile
1               5                   10                  15 ccc ctc gtc tgc ctc atc ctc cac gct tcc ctg tcc gac gcc cag ctc        96
Pro Leu Val Cys Leu Ile Leu His Ala Ser Leu Ser Asp Ala Gln Leu
                20                  25                  30 acc cct acc ttc tac gac aac tcc tgc cct aac gtc agc aac atc gtc       144
Thr Pro Thr Phe Tyr Asp Asn Ser Cys Pro Asn Val Ser Asn Ile Val
            35                  40                  45 cgc gac acc atc gtc aac gag ctg cgc tcc gac ccc cgt atc gcc gcc       192
Arg Asp Thr Ile Val Asn Glu Leu Arg Ser Asp Pro Arg Ile Ala Ala
        50                  55                  60 tcc atc ctc cgc ctc cac ttc cac gac tgc ttc gtc aac ggt tgc gac       240
Ser Ile Leu Arg Leu His Phe His Asp Cys Phe Val Asn Gly Cys Asp
65                  70                  75                  80 gct tcc atc ctc ctc gac aac acc acc agc ttc cgc acc gag aag gac       288
Ala Ser Ile Leu Leu Asp Asn Thr Thr Ser Phe Arg Thr Glu Lys Asp
                85                  90                  95 gcc ttc ggc aac gcc aac tcc gct cgc ggc ttc ccc gtc atc gac cgc       336
```

```
                Ala Phe Gly Asn Ala Asn Ser Ala Arg Gly Phe Pro Val Ile Asp Arg
                            100                 105                 110 atg aag gcc gcc gtc gag tcc gcc tgc cct cgc acc gtc agc tgc gcc          384
Met Lys Ala Ala Val Glu Ser Ala Cys Pro Arg Thr Val Ser Cys Ala
            115                 120                 125 gac ctc ctc acg atc gcc gcc cag cag tcc gtc acc ctc gcc ggt ggc          432
Asp Leu Leu Thr Ile Ala Ala Gln Gln Ser Val Thr Leu Ala Gly Gly
130                 135                 140 ccc tcc tgg cgt gtt cct ctc ggt cgc cgc gac tcc ctc cag gct ttc          480
Pro Ser Trp Arg Val Pro Leu Gly Arg Arg Asp Ser Leu Gln Ala Phe
145                 150                 155                 160 ctc gac ctc gcc aac gcc aac ctg ccc gct ccc ttc ttc acc ctg ccc          528
Leu Asp Leu Ala Asn Ala Asn Leu Pro Ala Pro Phe Phe Thr Leu Pro
                165                 170                 175 cag ctc aag gac tcc ttc cgc aac gtc ggc ctc aac cgc tcc tcc gac          576
Gln Leu Lys Asp Ser Phe Arg Asn Val Gly Leu Asn Arg Ser Ser Asp
            180                 185                 190 ctc gtt gcc ctc tcc ggc ggt cac acc ttc ggc aag aac cag tgc cgc          624
Leu Val Ala Leu Ser Gly Gly His Thr Phe Gly Lys Asn Gln Cys Arg
        195                 200                 205 ttc atc atg gac cgc ctc tac aac ttc tcc aac acc ggc ctc ccc gac          672
Phe Ile Met Asp Arg Leu Tyr Asn Phe Ser Asn Thr Gly Leu Pro Asp
210                 215                 220 ccc acc ctc aac acc acc tac ctg cag acc ctc cgc ggc ctc tgc ccc          720
Pro Thr Leu Asn Thr Thr Tyr Leu Gln Thr Leu Arg Gly Leu Cys Pro
225                 230                 235                 240 ctc aac ggc aac ctc tcc gcc ctc gtg gac ttc gac ctc cgc acc ccc          768
Leu Asn Gly Asn Leu Ser Ala Leu Val Asp Phe Asp Leu Arg Thr Pro
                245                 250                 255 acc atc ttc gat aac aag tac tac gtc aac ctg gag gag cag aag ggc          816
Thr Ile Phe Asp Asn Lys Tyr Tyr Val Asn Leu Glu Glu Gln Lys Gly
            260                 265                 270 ctc atc cag tcc gac cag gag ctg ttc tcc tcc ccc aac gcc acc gac          864
Leu Ile Gln Ser Asp Gln Glu Leu Phe Ser Ser Pro Asn Ala Thr Asp
        275                 280                 285 acg atc ccc ctg gtc cgc tcc ttc gcc aac tcc acc cag acg ttc ttc          912
Thr Ile Pro Leu Val Arg Ser Phe Ala Asn Ser Thr Gln Thr Phe Phe
290                 295                 300 aac gcc ttc gtc gag gcc atg gac cgc atg ggc aac atc acc ccc ctc          960
Asn Ala Phe Val Glu Ala Met Asp Arg Met Gly Asn Ile Thr Pro Leu
305                 310                 315                 320 acc ggc acc cag ggc cag atc cgc ctc aac tgc cgc gtc gtc aac tcc         1008
Thr Gly Thr Gln Gly Gln Ile Arg Leu Asn Cys Arg Val Val Asn Ser
                325                 330                 335 aac tcc tag                                                              1017
Asn Ser <210> SEQ ID NO 2
<211> LENGTH: 338
<212> TYPE: PRT
<213> ORGANISM: Artificial Sequence
<220> FEATURE:
<223> OTHER INFORMATION: Synthetic polypeptide encoded by synthetic
      polynucleotide having the base sequence of SEQ ID NO:1

<400> SEQUENCE: 2

Met His Phe Ser Ser Ser Thr Leu Phe Thr Cys Ile Thr Leu Ile
1               5                   10                  15

Pro Leu Val Cys Leu Ile Leu His Ala Ser Leu Ser Asp Ala Gln Leu
                20                  25                  30
```

```
Thr Pro Thr Phe Tyr Asp Asn Ser Cys Pro Asn Val Ser Asn Ile Val
        35                  40                  45

Arg Asp Thr Ile Val Asn Glu Leu Arg Ser Asp Pro Arg Ile Ala Ala
 50                  55                  60

Ser Ile Leu Arg Leu His Phe His Asp Cys Phe Val Asn Gly Cys Asp
 65                  70                  75                  80

Ala Ser Ile Leu Leu Asp Asn Thr Thr Ser Phe Arg Thr Glu Lys Asp
                 85                  90                  95

Ala Phe Gly Asn Ala Asn Ser Ala Arg Gly Phe Pro Val Ile Asp Arg
                100                 105                 110

Met Lys Ala Ala Val Glu Ser Ala Cys Pro Arg Thr Val Ser Cys Ala
            115                 120                 125

Asp Leu Leu Thr Ile Ala Ala Gln Gln Ser Val Thr Leu Ala Gly Gly
        130                 135                 140

Pro Ser Trp Arg Val Pro Leu Gly Arg Arg Asp Ser Leu Gln Ala Phe
145                 150                 155                 160

Leu Asp Leu Ala Asn Ala Asn Leu Pro Ala Pro Phe Phe Thr Leu Pro
                165                 170                 175

Gln Leu Lys Asp Ser Phe Arg Asn Val Gly Leu Asn Arg Ser Ser Asp
            180                 185                 190

Leu Val Ala Leu Ser Gly Gly His Thr Phe Gly Lys Asn Gln Cys Arg
        195                 200                 205

Phe Ile Met Asp Arg Leu Tyr Asn Phe Ser Asn Thr Gly Leu Pro Asp
210                 215                 220

Pro Thr Leu Asn Thr Thr Tyr Leu Gln Thr Leu Arg Gly Leu Cys Pro
225                 230                 235                 240

Leu Asn Gly Asn Leu Ser Ala Leu Val Asp Phe Asp Leu Arg Thr Pro
                245                 250                 255

Thr Ile Phe Asp Asn Lys Tyr Tyr Val Asn Leu Glu Glu Gln Lys Gly
            260                 265                 270

Leu Ile Gln Ser Asp Gln Glu Leu Phe Ser Ser Pro Asn Ala Thr Asp
        275                 280                 285

Thr Ile Pro Leu Val Arg Ser Phe Ala Asn Ser Thr Gln Thr Phe Phe
290                 295                 300

Asn Ala Phe Val Glu Ala Met Asp Arg Met Gly Asn Ile Thr Pro Leu
305                 310                 315                 320

Thr Gly Thr Gln Gly Gln Ile Arg Leu Asn Cys Arg Val Val Asn Ser
                325                 330                 335

Asn Ser
```

```
<210> SEQ ID NO 3
<211> LENGTH: 1014
<212> TYPE: DNA
<213> ORGANISM: Horseradish
<220> FEATURE:
<221> NAME/KEY: CDS
<222> LOCATION: (1)..(1014)

<400> SEQUENCE: 3
```

```
atg cat ttc tct tct tct tct act ttg ttc act tgt ata acc tta atc    48
Met His Phe Ser Ser Ser Ser Thr Leu Phe Thr Cys Ile Thr Leu Ile
 1               5                  10                  15 cca ttg gta tgt ctt att ctt cat gct tct ttg tct gat gct caa ctt    96
Pro Leu Val Cys Leu Ile Leu His Ala Ser Leu Ser Asp Ala Gln Leu
             20                  25                  30
```

```
acc cct acc ttc tac gac aat tca tgt cct aat gtc tct aac atc gta    144
Thr Pro Thr Phe Tyr Asp Asn Ser Cys Pro Asn Val Ser Asn Ile Val
         35                  40                  45 cgg gat act att gtc aat gag cta aga tca gac cct cgt att gcc gcg    192
Arg Asp Thr Ile Val Asn Glu Leu Arg Ser Asp Pro Arg Ile Ala Ala
 50                  55                  60 agc atc ctt cgt ctt cac ttc cac gac tgc ttt gtt aat ggt tgt gac    240
Ser Ile Leu Arg Leu His Phe His Asp Cys Phe Val Asn Gly Cys Asp
 65                  70                  75                  80 gca tcg atc ttg tta gac aac aca aca tca ttt cga aca gag aaa gat    288
Ala Ser Ile Leu Leu Asp Asn Thr Thr Ser Phe Arg Thr Glu Lys Asp
                 85                  90                  95 gcg ttt gga aac gca aac tcg gca aga gga ttt cca gtg att gat aga    336
Ala Phe Gly Asn Ala Asn Ser Ala Arg Gly Phe Pro Val Ile Asp Arg
            100                 105                 110 atg aaa gcc gcg gtg gag agt gca tgc cca aga acc gtt tca tgc gca    384
Met Lys Ala Ala Val Glu Ser Ala Cys Pro Arg Thr Val Ser Cys Ala
                115                 120                 125 gat ttg ctc acc att gca gct caa caa tct gtc act ttg gcg gga ggt    432
Asp Leu Leu Thr Ile Ala Ala Gln Gln Ser Val Thr Leu Ala Gly Gly
130                 135                 140 cct tct tgg aga gtt cct ttg ggc aga aga gat agc tta caa gca ttt    480
Pro Ser Trp Arg Val Pro Leu Gly Arg Arg Asp Ser Leu Gln Ala Phe
145                 150                 155                 160 ctg gat ctt gct aat gca aat ctt cca gct cca ttc ttc aca ctt cca    528
Leu Asp Leu Ala Asn Ala Asn Leu Pro Ala Pro Phe Phe Thr Leu Pro
                165                 170                 175 caa ctt aaa gac agc ttt aga aat gtt ggc ctc aac cgt tct tct gat    576
Gln Leu Lys Asp Ser Phe Arg Asn Val Gly Leu Asn Arg Ser Ser Asp
                180                 185                 190 ctc gtt gca ctg tcc ggg ggc cac aca ttt ggt aaa aat cag tgt cgg    624
Leu Val Ala Leu Ser Gly Gly His Thr Phe Gly Lys Asn Gln Cys Arg
            195                 200                 205 ttt att atg gac aga tta tac aac ttc agc aac acc ggt tta ccc gat    672
Phe Ile Met Asp Arg Leu Tyr Asn Phe Ser Asn Thr Gly Leu Pro Asp
210                 215                 220 cct act ctc aac act act tat ctc caa act ctt cgt gga cta tgt ccc    720
Pro Thr Leu Asn Thr Thr Tyr Leu Gln Thr Leu Arg Gly Leu Cys Pro
225                 230                 235                 240 ctc aat ggt aat cta agc gct ttg gtg gat ttt gat cta cgt acg cca    768
Leu Asn Gly Asn Leu Ser Ala Leu Val Asp Phe Asp Leu Arg Thr Pro
                245                 250                 255 acg att ttt gac aac aaa tac tat gtg aat ctc gaa gag caa aaa gga    816
Thr Ile Phe Asp Asn Lys Tyr Tyr Val Asn Leu Glu Glu Gln Lys Gly
                260                 265                 270 ctt atc caa agc gac caa gag ttg ttc tct agc ccc aat gcc act gac    864
Leu Ile Gln Ser Asp Gln Glu Leu Phe Ser Ser Pro Asn Ala Thr Asp
            275                 280                 285 aca atc cct ttg gtg aga tca ttt gct aat agc aca caa aca ttc ttc    912
Thr Ile Pro Leu Val Arg Ser Phe Ala Asn Ser Thr Gln Thr Phe Phe
290                 295                 300 aat gca ttt gtg gag gcg atg gat agg atg gga aac att aca cct ctt    960
Asn Ala Phe Val Glu Ala Met Asp Arg Met Gly Asn Ile Thr Pro Leu
305                 310                 315                 320 aca gga act caa gga cag atc agg ttg aat tgt agg gtg gtg aac tcc    1008
Thr Gly Thr Gln Gly Gln Ile Arg Leu Asn Cys Arg Val Val Asn Ser
                325                 330                 335 aac tct                                                            1014
Asn Ser
```

<210> SEQ ID NO 4
<211> LENGTH: 338
<212> TYPE: PRT
<213> ORGANISM: Horseradish

<400> SEQUENCE: 4

```
Met His Phe Ser Ser Ser Thr Leu Phe Thr Cys Ile Thr Leu Ile
1               5                   10                  15

Pro Leu Val Cys Leu Ile Leu His Ala Ser Leu Ser Asp Ala Gln Leu
            20                  25                  30

Thr Pro Thr Phe Tyr Asp Asn Ser Cys Pro Asn Val Ser Asn Ile Val
            35                  40                  45

Arg Asp Thr Ile Val Asn Glu Leu Arg Ser Asp Pro Arg Ile Ala Ala
50                  55                  60

Ser Ile Leu Arg Leu His Phe His Asp Cys Phe Val Asn Gly Cys Asp
65                  70                  75                  80

Ala Ser Ile Leu Leu Asp Asn Thr Thr Ser Phe Arg Thr Glu Lys Asp
                85                  90                  95

Ala Phe Gly Asn Ala Asn Ser Ala Arg Gly Phe Pro Val Ile Asp Arg
            100                 105                 110

Met Lys Ala Ala Val Glu Ser Ala Cys Pro Arg Thr Val Ser Cys Ala
            115                 120                 125

Asp Leu Leu Thr Ile Ala Ala Gln Gln Ser Val Thr Leu Ala Gly Gly
130                 135                 140

Pro Ser Trp Arg Val Pro Leu Gly Arg Arg Asp Ser Leu Gln Ala Phe
145                 150                 155                 160

Leu Asp Leu Ala Asn Ala Asn Leu Pro Ala Pro Phe Phe Thr Leu Pro
                165                 170                 175

Gln Leu Lys Asp Ser Phe Arg Asn Val Gly Leu Asn Arg Ser Ser Asp
            180                 185                 190

Leu Val Ala Leu Ser Gly Gly His Thr Phe Gly Lys Asn Gln Cys Arg
            195                 200                 205

Phe Ile Met Asp Arg Leu Tyr Asn Phe Ser Asn Thr Gly Leu Pro Asp
210                 215                 220

Pro Thr Leu Asn Thr Thr Tyr Leu Gln Thr Leu Arg Gly Leu Cys Pro
225                 230                 235                 240

Leu Asn Gly Asn Leu Ser Ala Leu Val Asp Phe Asp Leu Arg Thr Pro
                245                 250                 255

Thr Ile Phe Asp Asn Lys Tyr Tyr Val Asn Leu Glu Glu Gln Lys Gly
            260                 265                 270

Leu Ile Gln Ser Asp Gln Glu Leu Phe Ser Ser Pro Asn Ala Thr Asp
            275                 280                 285

Thr Ile Pro Leu Val Arg Ser Phe Ala Asn Ser Thr Gln Thr Phe Phe
290                 295                 300

Asn Ala Phe Val Glu Ala Met Asp Arg Met Gly Asn Ile Thr Pro Leu
305                 310                 315                 320

Thr Gly Thr Gln Gly Gln Ile Arg Leu Asn Cys Arg Val Val Asn Ser
                325                 330                 335

Asn Ser
```

<210> SEQ ID NO 5
<211> LENGTH: 39
<212> TYPE: DNA
<213> ORGANISM: Artificial Sequence
<220> FEATURE:

```
<223> OTHER INFORMATION: Synthetic primer sequence

<400> SEQUENCE: 5
cccggatcct gggacaagat gcacttctcc agctcctcc                              39

<210> SEQ ID NO 6
<211> LENGTH: 55
<212> TYPE: DNA
<213> ORGANISM: Artificial Sequence
<220> FEATURE:
<223> OTHER INFORMATION: Synthetic primer sequence

<400> SEQUENCE: 6
cccggatccc tagtgatggt gatgatggtg gtggtgggag ttggagttga cgacg           55

<210> SEQ ID NO 7
<211> LENGTH: 18
<212> TYPE: DNA
<213> ORGANISM: Artificial Sequence
<220> FEATURE:
<223> OTHER INFORMATION: Synthetic primer sequence

<400> SEQUENCE: 7
atggcaccac acccgacg                                                    18

<210> SEQ ID NO 8
<211> LENGTH: 18
<212> TYPE: DNA
<213> ORGANISM: Artificial Sequence
<220> FEATURE:
<223> OTHER INFORMATION: Synthetic primer sequence

<400> SEQUENCE: 8
ctatcgcagt agccgctc                                                    18

<210> SEQ ID NO 9
<211> LENGTH: 27
<212> TYPE: DNA
<213> ORGANISM: Artificial Sequence
<220> FEATURE:
<223> OTHER INFORMATION: Synthetic primer sequence

<400> SEQUENCE: 9
ggtctagact gcaggcactt ccaggca                                          27

<210> SEQ ID NO 10
<211> LENGTH: 30
<212> TYPE: DNA
<213> ORGANISM: Artificial Sequence
<220> FEATURE:
<223> OTHER INFORMATION: Synthetic primer sequence

<400> SEQUENCE: 10
ggtctagagc atgacgaata catatcaaac                                       30

<210> SEQ ID NO 11
<211> LENGTH: 29
<212> TYPE: DNA
<213> ORGANISM: Artificial Sequence
<220> FEATURE:
<223> OTHER INFORMATION: Synthetic primer sequence

<400> SEQUENCE: 11
gatatctgtg gggtttattg ttcagagaa                                        29
```

```
<210> SEQ ID NO 12
<211> LENGTH: 29
<212> TYPE: DNA
<213> ORGANISM: Artificial Sequence
<220> FEATURE:
<223> OTHER INFORMATION: Synthetic primer sequence

<400> SEQUENCE: 12
gatatcaggg tggagagtat atgatggta                                              29

<210> SEQ ID NO 13
<211> LENGTH: 29
<212> TYPE: DNA
<213> ORGANISM: Artificial Sequence
<220> FEATURE:
<223> OTHER INFORMATION: Synthetic primer sequence

<400> SEQUENCE: 13
ggcatttatg cacttctcca gctcctcca                                              29

<210> SEQ ID NO 14
<211> LENGTH: 46
<212> TYPE: DNA
<213> ORGANISM: Artificial Sequence
<220> FEATURE:
<223> OTHER INFORMATION: Synthetic primer sequence

<400> SEQUENCE: 14
ctagtgatgg tgatgatggt ggtggtggga gttggagttg acgacg                           46

<210> SEQ ID NO 15
<211> LENGTH: 30
<212> TYPE: DNA
<213> ORGANISM: Artificial Sequence
<220> FEATURE:
<223> OTHER INFORMATION: Synthetic primer sequence

<400> SEQUENCE: 15
gggaggcctg cgcatcatgc acttctccag                                             30

<210> SEQ ID NO 16
<211> LENGTH: 30
<212> TYPE: DNA
<213> ORGANISM: Artificial Sequence
<220> FEATURE:
<223> OTHER INFORMATION: Synthetic primer sequence

<400> SEQUENCE: 16
cccctcgagc taggagttgg agttgacgac                                             30

<210> SEQ ID NO 17
<211> LENGTH: 30
<212> TYPE: DNA
<213> ORGANISM: Artificial Sequence
<220> FEATURE:
<223> OTHER INFORMATION: Synthetic primer sequence

<400> SEQUENCE: 17
cccctcgagc taggagttgg agttgacgac                                             30

<210> SEQ ID NO 18
<211> LENGTH: 28
<212> TYPE: DNA
<213> ORGANISM: Artificial Sequence
<220> FEATURE:
<223> OTHER INFORMATION: Synthetic primer sequence
```

<400> SEQUENCE: 18
ggttaacctg agtagggccg ggagagga                                28

<210> SEQ ID NO 19
<211> LENGTH: 30
<212> TYPE: DNA
<213> ORGANISM: Artificial Sequence
<220> FEATURE:
<223> OTHER INFORMATION: Synthetic primer sequence

<400> SEQUENCE: 19
ggctgcagta aggtactcga gcaaaagctt                              30

<210> SEQ ID NO 20
<211> LENGTH: 39
<212> TYPE: DNA
<213> ORGANISM: Artificial Sequence
<220> FEATURE:
<223> OTHER INFORMATION: Synthetic primer sequence

<400> SEQUENCE: 20
gctattgaga agcgccagct caccccctacc ttctacgac                   39

<210> SEQ ID NO 21
<211> LENGTH: 21
<212> TYPE: DNA
<213> ORGANISM: Artificial Sequence
<220> FEATURE:
<223> OTHER INFORMATION: Synthetic primer sequence

<400> SEQUENCE: 21
ctaggagttg gagttgacga c                                       21

<210> SEQ ID NO 22
<211> LENGTH: 1017
<212> TYPE: DNA
<213> ORGANISM: Artificial Sequence
<220> FEATURE:
<223> OTHER INFORMATION: Synthetic polynucleotide sequence in which
      codon usage was adapted for Trichoderma
<220> FEATURE:
<221> NAME/KEY: CDS
<222> LOCATION: (1)..(1017)

<400> SEQUENCE: 22

```
atg cac ttc agc agc agc agc acc ctc ttc act tgc atc acc ctc atc      48
Met His Phe Ser Ser Ser Ser Thr Leu Phe Thr Cys Ile Thr Leu Ile
1               5                   10                  15 ccc ctc gtc tgc ctc atc ctc cac gcc agc ctc agc gac gcc cag ctc      96
Pro Leu Val Cys Leu Ile Leu His Ala Ser Leu Ser Asp Ala Gln Leu
            20                  25                  30 acc ccc acc ttc tac gac aac agc tgc ccc aac gtc agc aac atc gtc     144
Thr Pro Thr Phe Tyr Asp Asn Ser Cys Pro Asn Val Ser Asn Ile Val
        35                  40                  45 cgc gac acc atc gtc aac gag ctg cgc agc gac ccc cgc atc gcc gcc     192
Arg Asp Thr Ile Val Asn Glu Leu Arg Ser Asp Pro Arg Ile Ala Ala
    50                  55                  60 agc atc ctc cgc ctc cac ttc cac gac tgc ttc gtt aac ggc tgc gac     240
Ser Ile Leu Arg Leu His Phe His Asp Cys Phe Val Asn Gly Cys Asp
65                  70                  75                  80 gcc tcc atc ctc ctc gac aac acc acc agc ttc cgc acc gag aag gac     288
Ala Ser Ile Leu Leu Asp Asn Thr Thr Ser Phe Arg Thr Glu Lys Asp
                85                  90                  95 gcc ttc ggc aac gcc aac agc gct cgc ggc ttc ccc gtc atc gac cgc     336
Ala Phe Gly Asn Ala Asn Ser Ala Arg Gly Phe Pro Val Ile Asp Arg
```

```
Ala Phe Gly Asn Ala Asn Ser Ala Arg Gly Phe Pro Val Ile Asp Arg
            100                 105                 110 atg aag gcc gcc gtc gag agc gcc tgc cct cgc acc gtc agc tgc gcc      384
Met Lys Ala Ala Val Glu Ser Ala Cys Pro Arg Thr Val Ser Cys Ala
        115                 120                 125 gac ctc ctc act atc gcc gcc cag cag agc gtc acc ctc gcc ggt ggc      432
Asp Leu Leu Thr Ile Ala Ala Gln Gln Ser Val Thr Leu Ala Gly Gly
130                 135                 140 cct agc tgg cgc gtc cct ctc ggc cgc cgc gac agc ctc cag gct ttc      480
Pro Ser Trp Arg Val Pro Leu Gly Arg Arg Asp Ser Leu Gln Ala Phe
145                 150                 155                 160 ctc gac ctc gcc aac gcc aac ctg cct gcc ccc ttc ttc acc ctg ccc      528
Leu Asp Leu Ala Asn Ala Asn Leu Pro Ala Pro Phe Phe Thr Leu Pro
                165                 170                 175 cag ctc aag gac agc ttc cgc aac gtc ggc ctc aac cgc agc tcc gac      576
Gln Leu Lys Asp Ser Phe Arg Asn Val Gly Leu Asn Arg Ser Ser Asp
            180                 185                 190 ctc gtc gcc ctc tct ggc ggc cac acc ttc ggc aag aac cag tgc cgc      624
Leu Val Ala Leu Ser Gly Gly His Thr Phe Gly Lys Asn Gln Cys Arg
        195                 200                 205 ttc atc atg gac cgc ctc tac aac ttc agc aac acc ggc ctc ccc gac      672
Phe Ile Met Asp Arg Leu Tyr Asn Phe Ser Asn Thr Gly Leu Pro Asp
210                 215                 220 ccc acc ctc aac acc acc tac ctc cag acc ctc cgc ggc ctc tgc ccc      720
Pro Thr Leu Asn Thr Thr Tyr Leu Gln Thr Leu Arg Gly Leu Cys Pro
225                 230                 235                 240 ctc aac ggc aac ctc agc gcc ctc gtc gat ttc gac ctc cgc acc ccc      768
Leu Asn Gly Asn Leu Ser Ala Leu Val Asp Phe Asp Leu Arg Thr Pro
                245                 250                 255 acc atc ttc gat aac aag tac tac gtc aac ctc gag gag cag aag ggc      816
Thr Ile Phe Asp Asn Lys Tyr Tyr Val Asn Leu Glu Glu Gln Lys Gly
            260                 265                 270 ctc atc cag agc gac cag gag ctg ttc agc agc ccc aac gcc acc gac      864
Leu Ile Gln Ser Asp Gln Glu Leu Phe Ser Ser Pro Asn Ala Thr Asp
        275                 280                 285 acc atc ccc ctg gtc cgc agc ttc gcc aac tct acc cag acc ttc ttc      912
Thr Ile Pro Leu Val Arg Ser Phe Ala Asn Ser Thr Gln Thr Phe Phe
290                 295                 300 aac gcc ttc gtc gag gcc atg gac cgc atg ggc aac atc acc ccc ctc      960
Asn Ala Phe Val Glu Ala Met Asp Arg Met Gly Asn Ile Thr Pro Leu
305                 310                 315                 320 acc ggc acc cag ggc cag atc cgc ctc aac tgc cgc gtc gtc aac agc     1008
Thr Gly Thr Gln Gly Gln Ile Arg Leu Asn Cys Arg Val Val Asn Ser
                325                 330                 335 aac agc tag                                                         1017
Asn Ser
```

<210> SEQ ID NO 23
<211> LENGTH: 338
<212> TYPE: PRT
<213> ORGANISM: Artificial Sequence
<220> FEATURE:
<223> OTHER INFORMATION: Synthetic polypeptide encoded by synthetic
      polynucleotide having the base sequence of SEQ ID NO:22

<400> SEQUENCE: 23

```
Met His Phe Ser Ser Ser Thr Leu Phe Thr Cys Ile Thr Leu Ile
1               5                   10                  15

Pro Leu Val Cys Leu Ile Leu His Ala Ser Leu Ser Asp Ala Gln Leu
                20                  25                  30
```

Thr Pro Thr Phe Tyr Asp Asn Ser Cys Pro Asn Val Ser Asn Ile Val
            35                  40                  45

Arg Asp Thr Ile Val Asn Glu Leu Arg Ser Asp Pro Arg Ile Ala Ala
 50                  55                  60

Ser Ile Leu Arg Leu His Phe His Asp Cys Phe Val Asn Gly Cys Asp
 65                  70                  75                  80

Ala Ser Ile Leu Leu Asp Asn Thr Thr Ser Phe Arg Thr Glu Lys Asp
                 85                  90                  95

Ala Phe Gly Asn Ala Asn Ser Ala Arg Gly Phe Pro Val Ile Asp Arg
                100                 105                 110

Met Lys Ala Ala Val Glu Ser Ala Cys Pro Arg Thr Val Ser Cys Ala
                115                 120                 125

Asp Leu Leu Thr Ile Ala Ala Gln Gln Ser Val Thr Leu Ala Gly Gly
        130                 135                 140

Pro Ser Trp Arg Val Pro Leu Gly Arg Arg Asp Ser Leu Gln Ala Phe
145                 150                 155                 160

Leu Asp Leu Ala Asn Ala Asn Leu Pro Ala Pro Phe Phe Thr Leu Pro
                165                 170                 175

Gln Leu Lys Asp Ser Phe Arg Asn Val Gly Leu Asn Arg Ser Ser Asp
                180                 185                 190

Leu Val Ala Leu Ser Gly Gly His Thr Phe Gly Lys Asn Gln Cys Arg
        195                 200                 205

Phe Ile Met Asp Arg Leu Tyr Asn Phe Ser Asn Thr Gly Leu Pro Asp
        210                 215                 220

Pro Thr Leu Asn Thr Thr Tyr Leu Gln Thr Leu Arg Gly Leu Cys Pro
225                 230                 235                 240

Leu Asn Gly Asn Leu Ser Ala Leu Val Asp Phe Asp Leu Arg Thr Pro
                245                 250                 255

Thr Ile Phe Asp Asn Lys Tyr Tyr Val Asn Leu Glu Glu Gln Lys Gly
                260                 265                 270

Leu Ile Gln Ser Asp Gln Glu Leu Phe Ser Ser Pro Asn Ala Thr Asp
        275                 280                 285

Thr Ile Pro Leu Val Arg Ser Phe Ala Asn Ser Thr Gln Thr Phe Phe
        290                 295                 300

Asn Ala Phe Val Glu Ala Met Asp Arg Met Gly Asn Ile Thr Pro Leu
305                 310                 315                 320

Thr Gly Thr Gln Gly Gln Ile Arg Leu Asn Cys Arg Val Val Asn Ser
                325                 330                 335

Asn Ser

<210> SEQ ID NO 24
<211> LENGTH: 26
<212> TYPE: DNA
<213> ORGANISM: Artificial Sequence
<220> FEATURE:
<223> OTHER INFORMATION: Synthetic primer sequence

<400> SEQUENCE: 24
gggaggcctg cgcatcatgc acttca         26

<210> SEQ ID NO 25
<211> LENGTH: 36
<212> TYPE: DNA
<213> ORGANISM: Artificial Sequence
<220> FEATURE:
<223> OTHER INFORMATION: Synthetic primer sequence

<400> SEQUENCE: 25
cccgtcgacg ctgttgctgt tgacgacgcg gcagtt					36

<210> SEQ ID NO 26
<211> LENGTH: 1017
<212> TYPE: DNA
<213> ORGANISM: Artificial Sequence
<220> FEATURE:
<223> OTHER INFORMATION: Synthetic polynucleotide sequence in which
      codon usage was adapted for Trichoderma, Humicola and Aspergillus
<220> FEATURE:
<221> NAME/KEY: CDS
<222> LOCATION: (1)..(1017)

<400> SEQUENCE: 26

```
atg cac ttc tcc agc tcc tcc acc ctc ttc acg tgc atc acc ctc atc       48
Met His Phe Ser Ser Ser Ser Thr Leu Phe Thr Cys Ile Thr Leu Ile
1               5                   10                  15 ccc ctc gtc tgc ctc atc ctc cac gct tcc ctg tcc gac gcc cag ctg       96
Pro Leu Val Cys Leu Ile Leu His Ala Ser Leu Ser Asp Ala Gln Leu
            20                  25                  30 acc cct acc ttc tac gac aac tcc tgc cct aac gtc tcc aac atc gtc      144
Thr Pro Thr Phe Tyr Asp Asn Ser Cys Pro Asn Val Ser Asn Ile Val
        35                  40                  45 cgc gac acc atc gtc aac gag ctc cgc tcc gac ccc cgt atc gcc gcc      192
Arg Asp Thr Ile Val Asn Glu Leu Arg Ser Asp Pro Arg Ile Ala Ala
50                  55                  60 agc atc ctc cgc ctc cac ttc cac gac tgc ttc gtc aac ggt tgc gac      240
Ser Ile Leu Arg Leu His Phe His Asp Cys Phe Val Asn Gly Cys Asp
65                  70                  75                  80 gct tcc atc ctc ctc gac aac acc acc agc ttc cgc acc gag aag gac      288
Ala Ser Ile Leu Leu Asp Asn Thr Thr Ser Phe Arg Thr Glu Lys Asp
                85                  90                  95 gcc ttc ggc aac gcc aac tcc gct cgc ggc ttc ccc gtc atc gac cgc      336
Ala Phe Gly Asn Ala Asn Ser Ala Arg Gly Phe Pro Val Ile Asp Arg
            100                 105                 110 atg aag gcc gcc gtc gag tcc gcc tgc cct cgc acc gtc tcc tgc gcc      384
Met Lys Ala Ala Val Glu Ser Ala Cys Pro Arg Thr Val Ser Cys Ala
        115                 120                 125 gac ctc ctc acg atc gcc gcc cag cag tcc gtc acc ctc gcc ggt ggc      432
Asp Leu Leu Thr Ile Ala Ala Gln Gln Ser Val Thr Leu Ala Gly Gly
130                 135                 140 ccc agc tgg cgt gtt cct ctc ggt cgc cgc gac tcc ctc cag gct ttc      480
Pro Ser Trp Arg Val Pro Leu Gly Arg Arg Asp Ser Leu Gln Ala Phe
145                 150                 155                 160 ctc gac ctc gcc aac gcc aac ctg ccc gct ccc ttc ttc acc ctg ccc      528
Leu Asp Leu Ala Asn Ala Asn Leu Pro Ala Pro Phe Phe Thr Leu Pro
                165                 170                 175 cag ctc aag gac tcc ttc cgc aac gtc ggc ctc aac cgc tcc tcc gac      576
Gln Leu Lys Asp Ser Phe Arg Asn Val Gly Leu Asn Arg Ser Ser Asp
            180                 185                 190 ctc gtt gcc ctc tcc ggc ggt cac acc ttc ggc aag aac cag tgc cgc      624
Leu Val Ala Leu Ser Gly Gly His Thr Phe Gly Lys Asn Gln Cys Arg
        195                 200                 205 ttc atc atg gac cgc ctc tac aac ttc tcc aac acc ggc ctc ccc gac      672
Phe Ile Met Asp Arg Leu Tyr Asn Phe Ser Asn Thr Gly Leu Pro Asp
    210                 215                 220 ccc acc ctc aac acc acc tac ctg cag acc ctc cgc ggc ctc tgc ccc      720
Pro Thr Leu Asn Thr Thr Tyr Leu Gln Thr Leu Arg Gly Leu Cys Pro
225                 230                 235                 240 ctc aac ggc aac ctc tcc gcc ctc gtg gac ttc gac ctc cgc acc ccc      768
Leu Asn Gly Asn Leu Ser Ala Leu Val Asp Phe Asp Leu Arg Thr Pro
```

```
Leu Asn Gly Asn Leu Ser Ala Leu Val Asp Phe Asp Leu Arg Thr Pro
            245                 250                 255 acc atc ttc gat aac aag tac tac gtc aac ctg gag gag cag aag ggc     816
Thr Ile Phe Asp Asn Lys Tyr Tyr Val Asn Leu Glu Glu Gln Lys Gly
        260                 265                 270 ctc atc cag tcc gac cag gag ctg ttc tcc tcc ccc aac gcc acc gac     864
Leu Ile Gln Ser Asp Gln Glu Leu Phe Ser Ser Pro Asn Ala Thr Asp
            275                 280                 285 acg atc ccc ctg gtc cgc tcc ttc gcc aac tcc acc cag acg ttc ttc     912
Thr Ile Pro Leu Val Arg Ser Phe Ala Asn Ser Thr Gln Thr Phe Phe
        290                 295                 300 aac gcc ttc gtc gag gcc atg gac cgc atg ggc aac atc acc ccc ctc     960
Asn Ala Phe Val Glu Ala Met Asp Arg Met Gly Asn Ile Thr Pro Leu
305                 310                 315                 320 acc ggc acc cag ggc cag atc cgc ctc aac tgc cgc gtc gtc aac tcc    1008
Thr Gly Thr Gln Gly Gln Ile Arg Leu Asn Cys Arg Val Val Asn Ser
            325                 330                 335 aac tcc tag                                                        1017
Asn Ser
```

<210> SEQ ID NO 27
<211> LENGTH: 338
<212> TYPE: PRT
<213> ORGANISM: Artificial Sequence
<220> FEATURE:
<223> OTHER INFORMATION: Synthetic polypeptide encoded by synthetic
      polynucleotide having the base sequence of SEQ ID NO:26

<400> SEQUENCE: 27

```
Met His Phe Ser Ser Ser Ser Thr Leu Phe Thr Cys Ile Thr Leu Ile
1               5                   10                  15

Pro Leu Val Cys Leu Ile Leu His Ala Ser Leu Ser Asp Ala Gln Leu
            20                  25                  30

Thr Pro Thr Phe Tyr Asp Asn Ser Cys Pro Asn Val Ser Asn Ile Val
        35                  40                  45

Arg Asp Thr Ile Val Asn Glu Leu Arg Ser Asp Pro Arg Ile Ala Ala
    50                  55                  60

Ser Ile Leu Arg Leu His Phe His Asp Cys Phe Val Asn Gly Cys Asp
65                  70                  75                  80

Ala Ser Ile Leu Leu Asp Asn Thr Thr Ser Phe Arg Thr Glu Lys Asp
                85                  90                  95

Ala Phe Gly Asn Ala Asn Ser Ala Arg Gly Phe Pro Val Ile Asp Arg
            100                 105                 110

Met Lys Ala Ala Val Glu Ser Ala Cys Pro Arg Thr Val Ser Cys Ala
        115                 120                 125

Asp Leu Leu Thr Ile Ala Ala Gln Gln Ser Val Thr Leu Ala Gly Gly
    130                 135                 140

Pro Ser Trp Arg Val Pro Leu Gly Arg Arg Asp Ser Leu Gln Ala Phe
145                 150                 155                 160

Leu Asp Leu Ala Asn Ala Asn Leu Pro Ala Pro Phe Phe Thr Leu Pro
                165                 170                 175

Gln Leu Lys Asp Ser Phe Arg Asn Val Gly Leu Asn Arg Ser Ser Asp
            180                 185                 190

Leu Val Ala Leu Ser Gly Gly His Thr Phe Gly Lys Asn Gln Cys Arg
        195                 200                 205

Phe Ile Met Asp Arg Leu Tyr Asn Phe Ser Asn Thr Gly Leu Pro Asp
    210                 215                 220
```

-continued

```
Pro Thr Leu Asn Thr Thr Tyr Leu Gln Thr Leu Arg Gly Leu Cys Pro
225                 230                 235                 240

Leu Asn Gly Asn Leu Ser Ala Leu Val Asp Phe Asp Leu Arg Thr Pro
                245                 250                 255

Thr Ile Phe Asp Asn Lys Tyr Tyr Val Asn Leu Glu Glu Gln Lys Gly
            260                 265                 270

Leu Ile Gln Ser Asp Gln Glu Leu Phe Ser Ser Pro Asn Ala Thr Asp
        275                 280                 285

Thr Ile Pro Leu Val Arg Ser Phe Ala Asn Ser Thr Gln Thr Phe Phe
    290                 295                 300

Asn Ala Phe Val Glu Ala Met Asp Arg Met Gly Asn Ile Thr Pro Leu
305                 310                 315                 320

Thr Gly Thr Gln Gly Gln Ile Arg Leu Asn Cys Arg Val Val Asn Ser
                325                 330                 335

Asn Ser
```